(12) United States Patent
Marangoni

(10) Patent No.: US 11,154,502 B2
(45) Date of Patent: Oct. 26, 2021

(54) LECITHIN VESICLES FOR ORAL DELIVERY

(71) Applicant: CannaClear Inc., Whistler (CA)

(72) Inventor: Alejandro Marangoni, Puslinch (CA)

(73) Assignee: CannaClear Inc., Whistler (CA)

( * ) Notice: Subject to any disclaimer, the term of this patent is extended or adjusted under 35 U.S.C. 154(b) by 0 days.

(21) Appl. No.: 16/256,594

(22) Filed: Jan. 24, 2019

(65) Prior Publication Data

US 2020/0237666 A1 Jul. 30, 2020

(51) Int. Cl.
*A61K 9/127* (2006.01)
*A61K 31/352* (2006.01)
*A61K 47/22* (2006.01)
*A61K 47/24* (2006.01)

(52) U.S. Cl.
CPC .......... *A61K 9/1274* (2013.01); *A61K 9/1277* (2013.01); *A61K 31/352* (2013.01); *A61K 47/22* (2013.01); *A61K 47/24* (2013.01)

(58) Field of Classification Search
None
See application file for complete search history.

(56) References Cited

U.S. PATENT DOCUMENTS

| | | | |
|---|---|---|---|
| 4,532,089 A | 7/1985 | MacDonald et al. | |
| 5,173,219 A * | 12/1992 | Kim | A61K 9/1277 264/4.6 |
| 5,185,154 A | 2/1993 | Lasic et al. | |
| 6,312,719 B1 * | 11/2001 | Hope | A61K 9/127 424/450 |
| 6,855,277 B2 * | 2/2005 | Baker | A61K 9/1277 264/4.3 |
| 8,808,734 B2 | 8/2014 | Winnicki | |
| 10,052,303 B2 | 8/2018 | Winnicki | |
| 2011/0318406 A1 | 12/2011 | Eley et al. | |
| 2018/0344786 A1 * | 12/2018 | Thacker, Jr. | A61K 36/185 |

FOREIGN PATENT DOCUMENTS

| | | | |
|---|---|---|---|
| CA | 2461702 | 4/2003 | |
| EP | 3632410 A1 * | 8/2020 | ............. A61K 9/127 |
| WO | 2011115684 | 9/2011 | |
| WO | 2015068052 | 5/2015 | |

OTHER PUBLICATIONS

De Larco et al (Cancer Biology and Therapy, 2010, 9(5), 362-370). (Year: 2010).*
Whitehurst et al (Emulsifiers in Food Technology, Lecithins, Blackwell Publishing, 2004). (Year: 2004).*
International Search Report of PCT/CA2020/050086—dated Feb. 28, 2020.
Written Opinion of PCT/CA2020/050086—dated Feb. 28, 2020.
Sandeep Kalepu et al.: "Liposomal drug delivery system: A comprehensive Review"; Int. J. Dev. & Res.; Oct.-Dec. 2013, vol. 5, Issue 4; pp. 62-75—the whole document.
H.H. Hub et al.; "Preparation of large unilamellar vesicles"; FEBS letters; Apr. 1982, vol. 140, No. 2, pp. 254-256—the whole document.
Hiroshi Kikushi et al.; "A polyol dilution method for mass production of liposomes", Journal of Liposome Research; 1994, vol. 4, No. 1; pp. 71-91.
Ayelet Barenholz et al.; "Nano-liposome of crude soy lecithin are effective for cleaning fuel-contaminated sand and soils"; Expert Opinion on Environmental Biology, Jul. 11, 2016; vol. 5, No. 3; pp. 1-6.
M.J. Hope et al.;"Generation of multi lamellar and unilamellar phospholipid vesicles"; Chemistry and Physics of Lipids; 1986, vol. 40; pp. 89-107.
Bansal et al.—"Feasibility study of lecithin nanovesicles as spacers to improve the solubility of milk protein concentrate powder during storage", Dairy Sci. & Technol. (2017) 96: 861-872.

\* cited by examiner

*Primary Examiner* — Celeste A Roney
(74) *Attorney, Agent, or Firm* — Susan Tandan; Gowling WLG (Canada) LLP

(57) ABSTRACT

Giant multi-lamellar vesicles (GMVs) comprising lecithin are provided which are at least about 3 μm in size. Methods for preparing the GMVs, and for preparing large unilamellar vesicles (LUVs) from the GMVs, are provided, as well as methods for encapsulating cargo within the GMVs and LUVs. The present vesicles are useful for the oral delivery of encapsulated cargo.

27 Claims, 17 Drawing Sheets

A)

B)

LECITHIN VESICLES FOR ORAL DELIVERY

FIELD OF THE INVENTION

The present invention generally relates to vesicles prepared from lecithin, and in particular relates to vesicles useful for encapsulation of cargo for oral delivery.

BACKGROUND OF THE INVENTION

Phospholipid bilayer vesicles have a long history of use as bioactive delivery systems. Phospholipids are the natural building blocks of all biological membranes in nature, the outer layer of cells and subcellular organelles. Phospholipids are amphipathic (or amphiphilic) molecules which contain hydrophobic and hydrophilic parts. When exposed to either hydrophobic or hydrophilic environments, these molecules associate with each other such that hydrophilic or water-loving regions associate with other such regions, and hydrophobic or water-hating regions associate with other such regions. This molecular "phase separation" is the driving force for self-assembly and eventual supramolecular structure formation. Most phospholipids when dispersed/dissolved in water, self-assemble into bilayers, effectively creating a two-dimensional fluid where molecules display translational, rotational and transverse (flip-flop across monolayers) motions. These bilayers very seldom remain in an open and planar arrangement due to the high energy costs of the edges exposed to water, and thus tend to naturally close to form phospholipid vesicles.

As opposed to emulsions or micelles, these vesicles have a central watery lumen since they are effectively closed bilayers as shown in FIG. 1A. Artificially constructed phospholipid bilayer vesicles are referred to as liposomes. Interest in liposomes arises due to their ability to: i) encapsulate or entrap both hydrophilic and hydrophobic bioactive compounds (drugs, nutraceuticals, cosmeceuticals), ii) cross cell membranes and iii) transport these bioactives to specific, even targeted, locations within the human body. Hydrophobic compounds can be incorporated within the hydrophobic aliphatic fatty acid chains of the phospholipids, while hydrophilic compounds can be incorporated in the watery lumen of the liposome. Liposomes differ from micelles, which are also spherical structures, but which are instead composed of a monolayer of an amphiphile. Phospholipids usually do not form micelles, but lysophospholipids and fatty acids do form micelles.

Liposomes can be classified according to their size and lamellarity, i.e. the number of bilayers present in the liposome as shown in FIG. 1B. Liposomes usually range from 15 nm to 1000 nm (μm) in diameter. Within this range, further size categories are identified as set out in Table 1.

TABLE 1

Current classification of phospholipid vesicles according to size and lamellarity.

| Liposome Types | Size | Number of Lamellae |
|---|---|---|
| Small Unilamellar Vesicles (SUV) | 20 nm-100 nm | Single |
| Multivesicular Vesicles (MW) | 200 nm-~3 μm | Multiple |
| Large Unilamellar Vesicles (LUV) | 100 nm-400 nm | Single |
| Large Multilamellar Vesicles (MLV) | 200 nm-~3 μm | Multiple |
| Giant Unilamellar Vesicles (GUV) | 1 μm and Larger | Single |

Liposomes are frequently manufactured by first dissolving phospholipids in an organic solvent, such as chloroform, chloroform-methanol or even ethanol, depending on the type of phospholipid used. A clear lipid film is subsequently formed by removal of the solvent, and gentle hydration of this film eventually leads to formation of large, multilamellar vesicles (MLV). An MLV consists of more than one bilayer, e.g. concentric bilayers, creating a structure analogous to that of an onion. Each bilayer is separated from the next by water. SUVs are produced by disrupting MLVs or MVVs using sonication (agitation by sound-waves) or pH jump techniques, and possibly microfluidization. These high energy processes can yield SUVs. However, the SUVs are not stable for long periods of time without addition of specific stabilizers and will tend to form larger vesicles (LUVs). Storing SUVs at a temperature above their gel to liquid-crystalline phase transition temperature can help prevent formation of larger vesicles. This can be achieved most easily by selecting phospholipids that are unsaturated rather than saturated. To produce LUVs, extrusion through defined-pore size polycarbonate filters and microfluidization is used. Following several freeze-thaw cycles, an MLV or MVV phospholipid suspension is forced through polycarbonate filters at high pressures and temperatures above the gel to liquid-crystalline phase transition temperature, leading to the formation of liposomes with diameters similar to the size of the pores they were extruded through. This technique, if employed with pores of approximately 100 nm in diameter, allows for the formation of LUVs approximately 120 nm-140 nm in size. The size distribution achieved by this method is much more reproducible and narrower than that achieved through sonication. More modem disruption techniques include the use of high-pressure homogenizers, such as microfluidizers, where vesicles are passed 3-4 times through interaction chambers at pressures upwards of 30,000 PSI. Vesicles in the size range 70-100 nm can be achieved in this fashion.

Liposomes have largely been used by the pharmaceutical industry for drug delivery. Decreased drug toxicity, increased drug stability and targeted delivery are some of the main advantages of this encapsulation and delivery strategy. The useful size range of these structures for medical applications is between 50 nm and 250 nm, particularly for intravenous drug delivery. When injected into the circulatory system, liposome clearance is determined by the rate and extent of both drug release and uptake of liposomes by cells of the mononuclear phagocyte system (MPS), or reticuloendothelial system (RES). It has been reported that liposomes smaller than 100 nm interact less with plasma proteins, evade capture by the RES, have a longer half-life in the blood, and accumulate passively at tumoral sites. Conversely, it was found that larger liposomes were eliminated more rapidly from blood circulation and do not escape RES uptake. Besides the requirement for small liposome sizes, the pharmaceutical industry requires well-defined molecular structures and compositions. For this reason, phospholipids used in these applications are preferably highly purified and molecularly homogenous, rather than being natural mixtures extracted from whole tissue such as dipalmitoyl-phosphatidylcholine or egg phosphatidylcholine.

In the frenzy of creating smaller and smaller liposomes for intravenous medical applications and targeted delivery, for example, to tumors or specific tissues, the utility of multilamellar vesicles discovered by Alex Bangham has not fully been considered. While some elegant studies were conducted in the late 1980's to address the mechanism of liposome formation, the research did not progress past a certain point. A question that arose during this period was whether phospholipid vesicles could form spontaneously and whether liposomes could be considered thermodynamically stable. This thermodynamic stability would differentiate them from oil-in-water emulsions, which are kinetically stable, but not thermodynamically stable.

While size and purity are important for pharmaceutical-grade liposomes, liposome characteristics required for oral delivery are not as stringent, particularly in foods. Liposomes are usually destroyed once they reach or exit the stomach and enter the small intestine. The harsh acidic environment and shear in the stomach, and the bile salts and enzymatic attack in the small intestine, are no match for a liposome. The liposome and its contents are integrated into the digestive system structures at this point. The size of the liposome, thus, is not as important in this case. Moreover, since these liposomes are used as food, there is no need to use high purity phospholipids for this application.

Although liposomes may be prepared with several polar lipid combinations, most work has been done with phosphatidylcholine. The reason for the popularity of phosphatidylcholine is because it is easy to solvent-fractionate from other phospholipids (ethanol-soluble) and purify, it is the most abundant phospholipid in biological membranes, and it forms stable liposomes readily and reproducibly. Moreover, the saturated versions of this phospholipid are preferred due to their oxidative stability and tendency to form lamellar mesophases, which are the core structure in a phospholipid bilayer. A drawback, however, is its high cost.

Interestingly, no natural system contains only phosphatidylcholine. Biological membranes are composed of complex mixtures of large numbers of polar lipids and proteins. Lecithin is technically a natural mixture of phospholipids extracted from biological tissue. For example, many plant membranes contain equal amounts of phosphatidylcholine, phosphatidylethanolamine and phosphatidylinositol. Other commonly found phospholipids include the single-chain version of the different phospholipids, the lyso-phosphatides, as well as phosphatidic acid. However, lecithin is often equated with only the phosphatidylcholine component of membranes.

Thus, it would be desirable to develop a novel liposome or vesicle designed for oral delivery.

SUMMARY OF THE INVENTION

Novel multi-lamellar vesicles comprising lecithin have now been developed which are suitable for use to orally deliver cargo.

Accordingly, in one aspect of the invention, multi-lamellar vesicles comprising lecithin are provided which are greater than 3 μm in size.

In another aspect, a method of preparing multi-lamellar vesicles which are greater than 3 μm in size is provided comprising the step of mixing lecithin in a buffer until fully dispersed.

In another aspect, a method of preparing large unilamellar vesicles is provided comprising the step of exposing multi-lamellar vesicles comprising lecithin which are greater than 3 μm in size to mixing for a sufficient period of time.

These and other aspects of the invention will become apparent from the detailed description that follows by reference to the following figures.

DETAILED DESCRIPTION OF THE INVENTION

Figure 1:
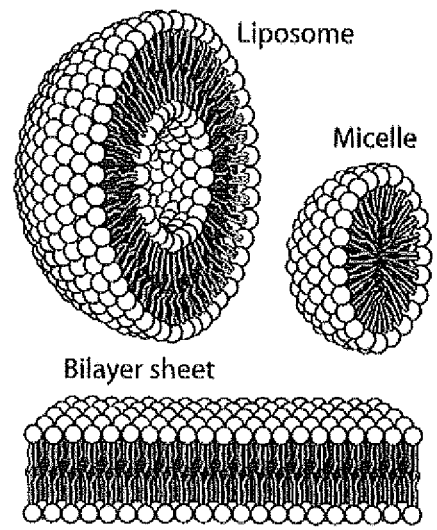
FIG. 1 is a schematic illustrating a liposome, micelle and phospholipid bilayer (A), and various types of liposomes according to size and lamellarity (B)
Figure 1:
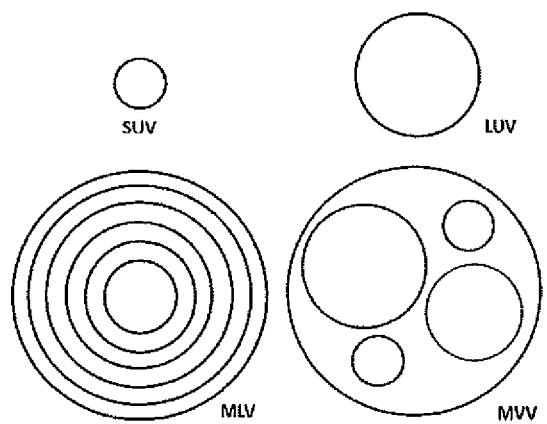

Multi-lamellar vesicles comprising lecithin are provided which are greater than 3 µm in size, e.g. referred to herein as giant multi-lamellar vesicles or GMVs.

The vesicles are made of lecithin which comprises a mixture of glycerophospholipids including one or more of a phosphatidylcholine, phosphatidylethanolamine, phosphatidylinositol, phosphatidylserine and phosphatidic acid. Examples of each include dilinoleylphosphatidylcholine, dilinoleylphosphatidylethanolmine, dilinoleyl-phosphatidylinositol, dilinoleylphosphatidylserine, dilinoleylphosphatidic acid, dioleylphosphatidylcholine, dioleylphosphatidylethanolamine, dioleylphosphatidylinositol, dioleylphosphatidylserine, dioleylphosphatidic acid, 1-oleyl-2-linoleylphosphatidylcholine, 1-oleyl-2-linoleylphosphatidylethanolamine, 1-oleyl-2-linoleylphosphatidylinositol, 1-oleyl-2-linoleylphosphatidylserine, 1-oleyl-2-linoleylphosphatidic acid, dipalmitoylphosphatidylcholine, dipalmitoylphosphatidylethanolamine, dipalmitoylphosphatidylionsitol, dipalmitoylphosphatidylserine, dipalmitoylphosphatidic acid, combinations of linolenic, linoleic, oleic, palmitic, stearic fatty, behenic, crucic, myristic, lauric, capric, caproic and caprylic fatty acids at positions sn-1 and sn-2 on each different phospholipid backbone (i.e. on the backbone of phosphatidylcholine, phosphatidylethanolamine, phosphatidylinositol, phosphatidylserine and phosphatidic acid). The lecithin may also include small amounts of glycolipids, carbohydrates and/or sterols.

In one embodiment, the lecithin comprises at least a phosphatidylcholine and a phosphatidylethanolamine in which the phosphatidylcholine to phosphatidylethanolamine (PC:PE) ratio is 0.5 to 5 PC:PE, preferably the PC:PE ratio is greater than 1 or greater than 1.5. In addition, the lecithin comprises less than 10 wt % of phosphatidic acid and less than 5% lysophosphatides, and preferably comprises less than 5 wt % phosphatidic acid and lysophosphatides combined, or no significant amount of phosphatidic acid and lysophosphatides, i.e. less than 1 wt %. Both phosphatidic acid and lysophosphatides are by-products of phospholipid degradation and have deleterious effects on phospholipid bilayer stability. Lysophosphatides are strong micellar phase formers while phosphatidic acid has a strong tendency to bind to metals, such as calcium, and form insoluble complexes. Thus, lecithin for use to prepare GMVs may comprise phosphatidylcholine in an amount in the range of about 15-50 wt % phosphatidylcholine, preferably 20-30 wt %, and about 10-25 wt % phosphatidylethanolatnine, preferably 10-15 wt %.

Sources of lecithin for use to prepare the present vesicles is not particularly limited. Sources include, but are not limited to, egg yolk, and vegetable sources, e.g. oilseeds such as sunflower, soybean, nuts and whole grains. Preferable are lecithins from vegetable sources, and most preferable are organically sourced lecithins. Lecithin is readily commercially available.

The present vesicles are prepared by mixing lecithin in a buffer until fully dispersed. The lecithin is dispersed in the buffer in an amount in the range of about 2-20% (w/w), preferably 5-15% (w/w) such as 10% (w/w). Generally, the lecithin dissolves in the buffer with mixing for at least about 15-60 minutes at a selected temperature, e.g. ranging from about 4° C. to about 75° C., preferably around 60° C., which enhances hydration and prevents microbial growth. Examples of suitable buffers include acidic, basic or neutral buffers. Thus, suitable buffers include, but are not limited to phosphate, citrate, malate, or other suitable biological buffer. Buffer may be used in a concentration range of 0.01-0.1 M.

In one embodiment an acidic buffer is used to dissolve the lecithin which advantageously provides the vesicles with microbial stability. Acidic buffer will generally comprise a weak acid, such as citric acid, ethanoic or acetic acid, lactic acid or phosphoric acid, and a salt of the acid, e.g. a sodium or potassium salt. The pH of the acidic buffer will be a pH that is greater than or equal to the pK of the phosphate group of the phospholipid within the lecithin, or a pH at which there is electrostatic stabilization of the mixture against flocculation and coalescence. Thus, the pH may be less than the pK of the phosphate of a phosphatidylcholine or phosphatidylethanolamine since these have a charged quaternary amine or protonated primary amine, respectively, which provides the necessary electrostatic stabilization. Preferably, the pH of the buffer is less than 4.5, but greater than 2.5, and more, preferably the pH is about 3-4.5.

The resulting multi-lamellar vesicles, or GMVs, are greater than 3 µm in size, preferably greater than 4 or 5 µm in size and may be less than 10 µm in size. The present vesicles are advantageously stable in a liquid crystalline state over a temperature range of 0-90° C.

The present vesicles may be modified to incorporate water soluble or fat soluble cargo. Water soluble cargo is entrapped in the lumen of the vesicles, while fat soluble cargo is captured in the vesicle membrane. Thus, the vesicles are useful to deliver a various types of cargo, from small molecule to macromolecule such as proteins, nucleic acids (DNA or RNA), hormones, polysaccharides, glycoproteins, tocopherols, sterols, and other naturally occurring or synthetic small or macromolecules, including both hydrophilic or hydrophobic molecules.

The vesicles may include a load equivalent to a mass ratio of the selected cargo to lecithin of at least 1:5, preferably 1:4 or less, such as 1:2 cargo to lecithin.

In one embodiment, the vesicles are modified to incorporate one or more cannabinoids. Examples include, but are not limited to, cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), cannabidivarin acid (CBDVA), cannabinovarin (CBNV), cannabinodiol (CBDL), cannabicyclol (CBL), cannabielsoin (CBE), cannabitriol (CBT), cannabivarin (CBV), cannabichromevarin (CBCV), cannabigerol monoethyl ether (CBGM), tetrahydrocannabinols (THC), tetrahydrocannabivarin (THCV), naphthoylindoles such as JWH-018, JWH-073, JWH-398, JWH-200, JWH-081, 4-methyl-JWH-073, JWH-015, JWH-122, JWH-220, JWH-019, JWH-007; phenylacetylindoles such as JWH-250 and JWH-203; benzoylindoles such as RCS-4, AM-694 and WIN 48,098; cyclohexylphenoles such as CP 47,497-C8 and CP 47,497; HU-210; terpenes (e.g. myrcene, beta caryophyllene, pinene, limonene, terpinolene, humulene, nerolidol, linalool, ocimene, guaiol, bisabolol, alpha phellandrene, cadinene, camphene, camphor, citral, citronellol, delta 3-carene, eucalyptol, eugenol, gamma terpinene, geraniol, humulene, nerol, nerolidol, ocimene, para-cymene, phytol, pulegone, terpineol and valencene) and pharmaceutically acceptable salts thereof.

For cargo that is susceptible to oxidation such as cannabinoids, it may be desirable for the vesicles to also include an antioxidant. In one embodiment, a phenolic antioxidant is used. Non-limiting examples of suitable phenolic antioxidants are tert-butyl hydroxy quinone (TBHQ), butylated hydroxy toluene (BHT), butylated hydroxyl anisole (BHA), propyl gallate (PG), a tocopherol and mixtures thereof.

Vesicles incorporating selected cargo may be prepared by combining cargo dissolved in a solvent with lecithin dispersed in a buffer (e.g. already formed vesicles, i.e. GMVs) and mixing for a period of time sufficient for uptake of the cargo by the vesicles. For example, water soluble cargo may be dissolved in an aqueous solvent and combined with the lecithin vesicle mixture. Following mixing and uptake of the cargo into the vesicle lumen, entrapment of the cargo may be enhanced by repeated freeze-thaw cycles followed by homogenization, filtration, sonication and pH Jump. To entrap hydrophobic cargo, the cargo is first dissolved in an appropriate solvent, for example, an alcohol such as ethanol, propanol or butanol, or a stronger organic solvent such as chloroform, if required (e.g. for lipophilic cargo). The dissolved hydrophobic cargo solution is then combined with the vesicles, which may optionally be heated. The cargo solution is generally added very slowly, e.g. a drop at a time, to the vesicle mixture to entrap the hydrophobic cargo within the phospholipid bilayers of the vesicle and to prevent the formation of undesirable aggregates. The method is generally conducted at increased temperature to facilitate cargo incorporation, for example, a temperature in the range of between 55-75° C., e.g. 60-70° C.

In another embodiment, large unilamellar vesicles (LUVs) may be prepared. LUVs are about 100-400 nm in size. LUVs may be prepared by exposing giant multi-lamellar vesicles to mixing, for example, mixing at 10,000-25,000 rpms for a period of time to shear GMVs to yield LUVs. As one of skill in the art will appreciate, the greater the rate of mixing, the less time required to form LUVS. Thus, using a mixing rate of 20,000-25,000 rpms, LUVs can be prepared from GMVs within about 15 minutes or less, e.g. 5 minutes. Using a mixing rate of 10,000 rpms increases the time to yield LUVs, e.g. 30-60 minutes. In one embodiment, rotor-stator mixing may be used to form the LUVs from the GMVs at various rpms.

LUVs comprising cargo may also be prepared. The selected cargo is dissolved in an appropriate solvent as described above. The dissolved cargo may be combined with GMVs and then subjected to mixing to form cargo-containing LUVs. Alternatively, the dissolved cargo may be added very slowly (e.g. a drop at a time) with mixing to already formed LUVs to form cargo-containing LUVs. Combining the cargo with GMVs or LUVs may be conducted at increased temperature, for example, a temperature in the range of between 55-75° C., in order to facilitate incorporation of the cargo into the vesicles. Specifically, the increased temperature aids evaporation of the solvent from the cargo, which forces uptake of the cargo by partitioning into the phospholipid bilayer of the vesicle.

Thus, according to aspects of the present invention, GMVs and LUVs are provided in an aqueous suspension which exhibit structural stability. Structural stability is evident due to the extended lifespan of the vesicles. In addition, the vesicles are readily prepared in an acidic solution which prevents the growth of pathogenic and spoilage bacteria, thereby providing a product with enhanced anti-microbial properties.

The present vesicles provided in aqueous solution are useful for the oral delivery of cargo, including small and macromolecules which may be either hydrophilic or hydrophobic. Thus, the vesicles may be provided for consumption in a beverage, including both hot and cold beverages, or may be combined with other edibles as the liquid component thereof.

Embodiments of the invention are described by reference to the following specific examples which are not to be construed as limiting.

Example 1. Computer Simulation of the Incorporation of Cannabinol into 1-stearoyl-2-oleyl-phosphatidylcholine Bilayers Atomic scale molecular mechanics computer simulation of the incorporation of cannabinol in phospholipid bilayers was conducted. For these atomistic simulations, two programs were used, ChemSite Pro version 10.5 (Copyright David Michael, Ph.D) and Molecular Modelling Pro Plus (MMP+) version 8.1.40 (Norgwyn Montgomery Software Inc, James A. Quinn, lead programmer). Under ChemSite, the "Build Lipid" function was used which had already formed 1-stearoyl-2-oleyl-phosphatidylcholine (SOPC) bilayers in the database. This constituted the phospholipid bilayer, the main structural component of a phospholipid vesicle. The bilayer was made of 8 SOPC molecules and 32 water molecules (one water layer). The simulation conditions were as follow:

Time step: 1
Total time: 10,000 ps
Bath temperature: 300K
Replay sampling period: 200
Equilibration steps: 200
NBI list refresh period: 20
Cutoff Distance: 7 Å
Initial lipid separation: 7 Å
Periodic Boundaries: 70 Å×15 Å×15 Å
No implicit solvent
Generalized Born solvation model GBV
Heat bath relaxation time (fs): 500
No other constraints The periodic boundary conditions were critical to this simulation. Without them, the simulations gave erroneous and erratic results and molecules would gradually migrate away from each other. The simulation was carried out as follows. First, the SOPC bilayer was built and its energy minimized within ChemSite using the default Amber minimization. Many characteristics were determined but the focus was on the total energy of the system. Once the first, empty, bilayer structure was minimized, one cannabinol molecule was introduced within the fatty acid chains of the bilayer. The structure was minimized containing the cannabinol molecule, and the minimum energy determined. This process was repeated up to the incorporation of 6 cannabinol molecules within the 8 SOPC molecule bilayer.

Figure 2:
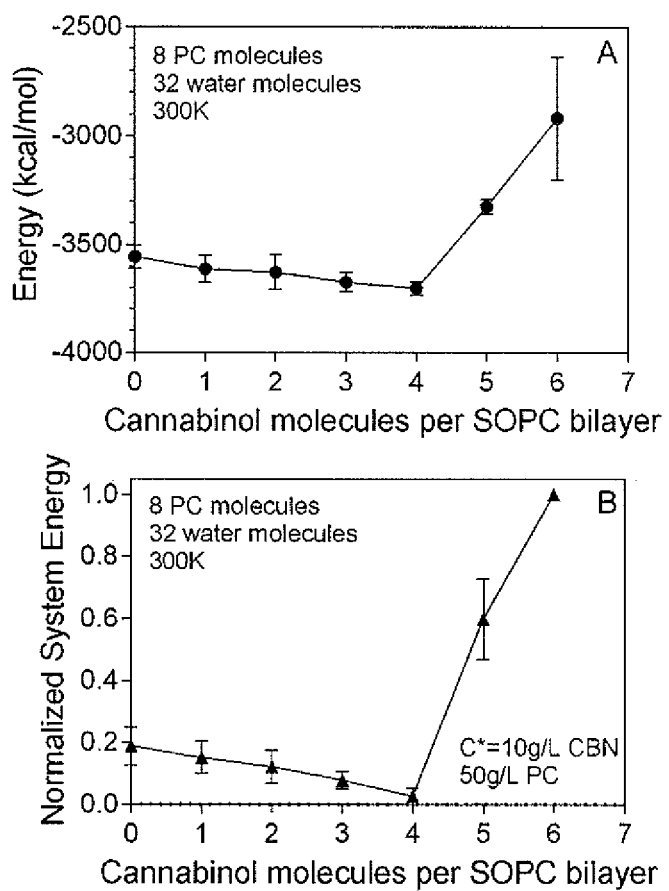
FIG. 2 illustrates atomic scale molecular mechanics simulations of the incorporation of cannabinol into a 1-palmitoyl, 2-oleyl phosphatidylcholine (POPC) phospholipid bilayer in terms of energy (A) and normalized system energy (B), as well as a schematic of the incorporation.
Figure 2:
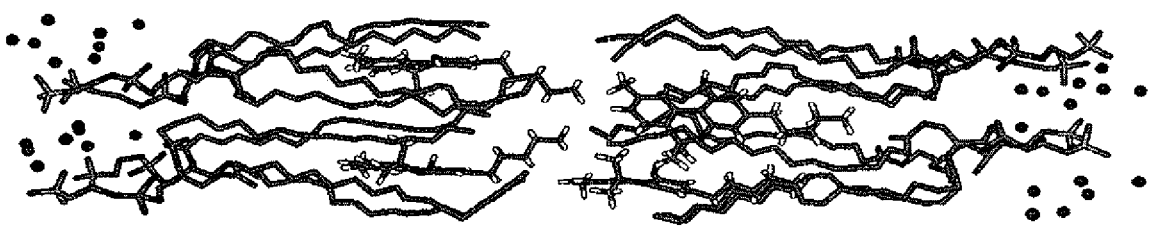

This simulation was replicated 6 times and means and standard errors reported in FIG. 2 which clearly shows how incorporation of more than 4 cannabinol molecules caused a large increase in the system's energy. The result were reproducible and interpreted as a destabilization of the bilayer if more than 4 cannabinol molecules were present within an 8 phospholipid bilayer corresponding to a 1:2 mol:mol ratio. One very interesting observation is that the incorporation of cannabinol at lower concentrations stabilizes the bilayer slightly as evidenced by a gradual decrease in the system's energy upon incorporation of 4 cannabinol molecules (2:1 mol:mol ratio). FIG. 2 shows the system's energy (FIG. 2A), the normalized system's energy (FIG. 2B) and the final minimized structure of cannabinol within SOPC bilayers, with water shown as the red circles (FIG.

2C). These studies suggest that cannabinol can be encapsulated within phospholipid vesicles up to a 2:1 mol:mol phospholipid:cannabinol content.

Example 2. Spontaneous, Thermodynamically Stable Giant Multilamellar Vesicles (sGMV)

A multicomponent phospholipid and glycolipid mixture was used for the spontaneous formation of thermodynamically stable vesicles. The soybean lecithin, Phospholipon20 (Lipoid GmbH, Ludwigshafen, Germany) and sunflower lecithin, Sunlec25 (Perimondo, New York, N.Y., USA) were used. Phosphatidylcholine content is denoted by the number in the lecithin name.

The phospholipid and fatty acid composition of these samples is set out in Table 2. Phospholipid content was provided by the manufacturers. Fatty acid composition was determined as follows. An Agilent 6890-series gas chromatography (Agilent Technologies, Inc., Wilmington, Del., USA) with a 7683-series auto-sampler was used to determine the fatty acid composition of samples. A GC column, BPX70 (SGE Inc. Austin, Tex., USA), 60 m×0.22 mm internal diameter with a 0.25 μm film thickness, was used. The oven temperature was programmed to increase from 110° C. to 230° C. (4° C./min) and was maintained at 230° C. for 18 minutes. The injector was set at 250° C. and operated at 20.1 psi with a flow of 17.7 mL/min. High-purity helium, a carrier gas, was flowed at an average velocity of 25 cm/s. A flame ionization detector was set at 255° C. with 450 mL/min air and 50 mL/min helium flow rate. The patterns obtained were analyzed using Open LAB software (Agilent Technologies). Fatty acid composition was determined by comparing retention times of the peaks to standards. Values are reported as relative mass ratios.

TABLE 2

Phospholipid and fatty acid composition of the lecithins used in this work.

| Phospholipid | Sunlec25 Sunflower Weight % | Phospholipon20 Soybean Weight % |
| --- | --- | --- |
| Phosphatidylcholine | 25 | 24 |
| Phosphatidylinositol | 29 | 15 |
| Phosphatidylethanolamine | 11 | 22 |
| Phosphatidic Acid | 6 | 7 |
| Minor phospholipids | 4 | 5 |
| Lysophosholipids | 0 | 3 |
| Glycolipids | 15 | 15 |
| Fatty acid | Weight % | Weight % |
| 16:0 | 17.6 | 18.9 |
| 18:0 | 4.1 | 4.0 |
| 18:1 | 11.1 | 9.7 |
| 18:2 | 64.7 | 58.8 |
| 18:3 | n.d | 6.6 |

The fatty acid composition was very similar between the sunflower and soybean lecithins, except for the higher linolenic acid (18:3) content of soybean lecithin. In terms of phospholipid composition, both sunflower and soybean have similar phosphatidylcholine contents, while the phosphatidylethanolamine content of soybean lecithin is about 2× higher than that of sunflower lecithin (22% vs. 11%).

The lecithin powders were dispersed at a 10% (w/w) level in 0.1M citric acid buffer, pH 4 at 30° C. The powder dispersions were gently stirred with an overhead paddle mixer at 200 rpm for 18 hours. All the powder dissolved/dispersed, and the dispersion was analyzed.

First, a standard estimation of the size of the structures created was performed. Particle size distribution determination was carried out via static light scattering using a Mastersizer 2000 (Malvern Instruments Ltd., UK) equipped with a Hydro 2000SM small volume sample dispersion unit. The refractive index of the suspended particles was assumed to be similar to that of phospholipid, and for the continuous phase, deionized water. Refractive index values of 1.42 and 1.33 were used for the dispersed and continuous phases, respectively. Sample was added until an initial obscuration of ~15% was reached. Each measurement was carried out in triplicate, and the average size distribution was reported.

Figure 3:
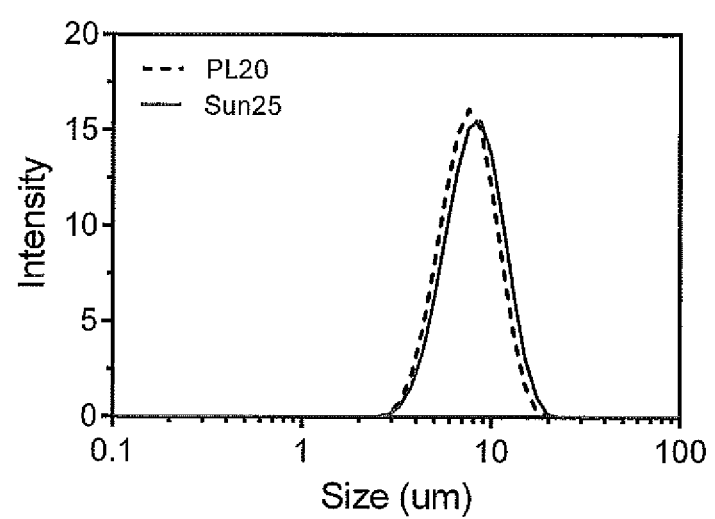
FIG. 3 graphically illustrates the size distribution of spontaneously formed giant phospholipid vesicles from soybean lecithin (PL20) and sunflower lecithin (Sun25) in 0.1M citrate buffer, pH 4.3.

The result of this analysis is presented in FIG. 3. As shown, a relatively narrow size monomodal distribution was obtained without any large aggregates or small structures. This structure formed spontaneously. The size of these phospholipid vesicles was 6.66 (+/−0.07) μm for Phospholipon20 and 7.44 (+/−0.29) μm for Sunlec25. For Phospolipon 20 the span of the distribution was 0.856, while for Sunlec25 it was 0.894.

Phospholipid vesicle structures were then characterized by bright-field microscopy (model DM RXA 2, Leica Microsystems Wetzlar GmbH, Wetzlar, Germany). Dispersions were prepared by 10:1 (v/v) dilution in deionized water, and ~10 μl were pipetted onto a microscope slide prior to applying a glass coverslip. For all images, a 40× objective was used, and the images were captured with a digital camera (Retiga 1300i, Qlmaging, Surrey, BC, Canada) using the Velocity software package (version 6.2.1; PerkinElmer, Woodbridge, ON, Canada). Images acquired were converted to grayscale and levels adjusted automatically using Adobe Photoshop CS5 (Adobe, San Jose, Calif., USA).

Figure 4:
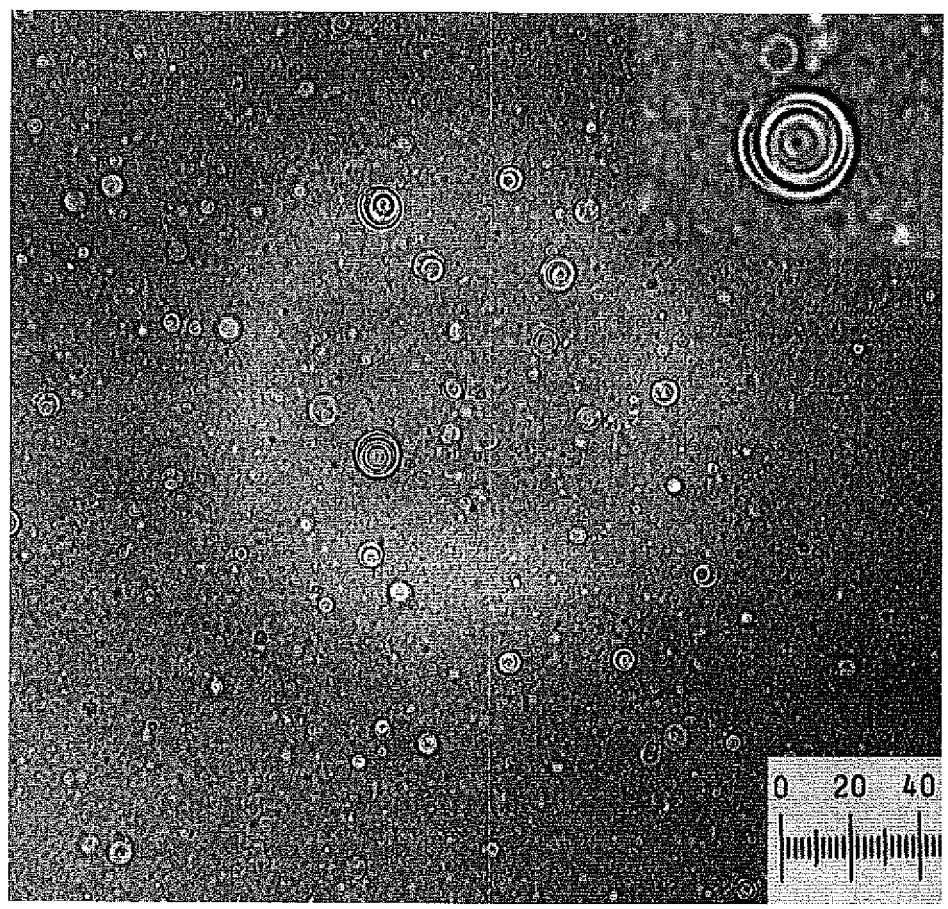
FIG. 4 illustrates a light micrograph of soybean lecithin giant multilamellar vesicles in 0.1M citrate butter, pH 4.3.
Figure 5:
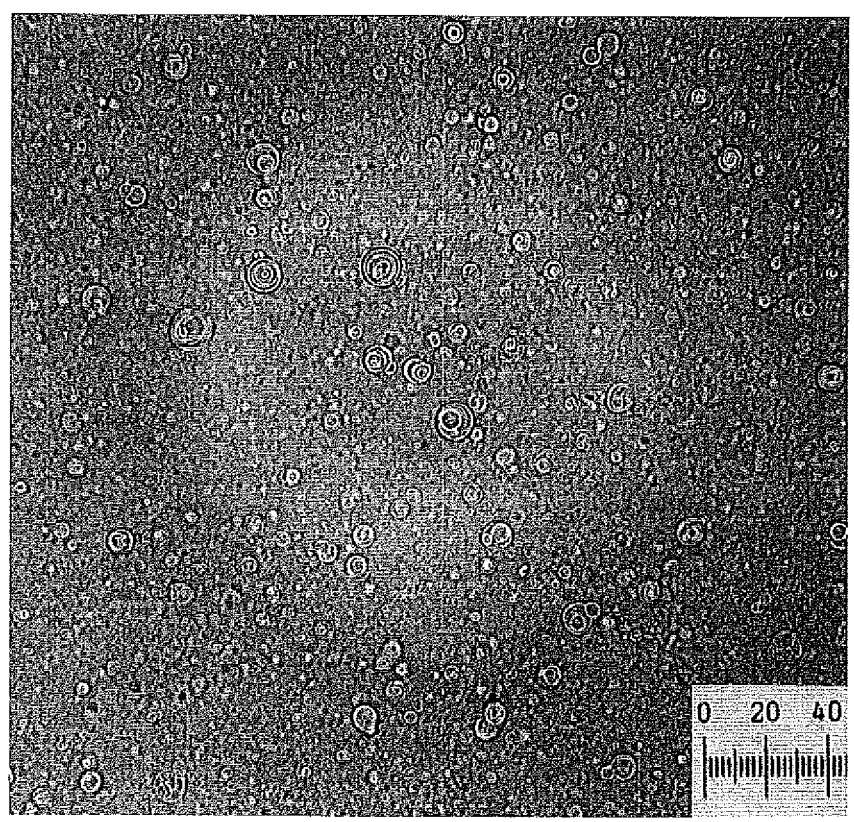
FIG. 5 illustrates a light micrograph of sunflower lecithin giant multilamellar vesicles in 0.1M citrate butter, pH 4.3.

Large vesicles of diameters comparable to that obtained by light scattering were observed, e.g. >6 μm. Moreover, it was also determined that these spontaneously formed vesicles were multilamellar for both soybean (FIG. 4) and sunflower (FIG. 5) lecithin. Thus, the vesicles formed may be classified as spontaneous Giant Multilamellar Vesicles, or sGMVs.

The thermal behavior of the vesicles was also characterized to determine if a phase transition from gel phase to liquid crystalline state existed in the temperature range of interest, namely, just above freezing to 90° C. Thermal behavior was evaluated using a differential scanning calorimeter, the DSC 1 instrument (Mettler-Toledo, Mississauga, ON, Canada). Approximately 10 mg of sample was placed into an aluminum DSC pan and hermetically sealed. Thermograms were obtained using a heating/cooling cycle between 25° C. to 90° C. at a rate of 5° C./min, with a 3 min isothermal period between the dynamic stages. Curves were evaluated using the Star Software (Mettler-Toledo) provided with the DSC unit.

Figure 6:
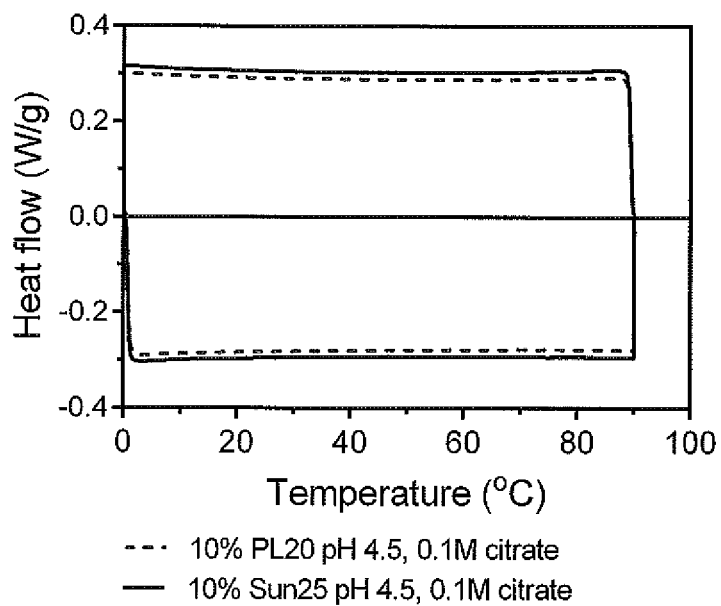
FIG. 6 illustrates differential scanning calorimetric scans of the spontaneous giant multilamellar vesicle, both heating (endothermic, negative heat flows) and cooling (exothermic, positive heat flows)

Results from this analysis are shown in FIG. 6. Negative (endothermic) heat flows correspond to heating while positive (exothermic) heat flows correspond to cooling. No thermal transition was evident at all. This is important since vesicles manufacture usually takes place in the liquid crystalline state. Moreover, vesicles are generally more stable in their liquid crystalline state, rather than in their gel state. This is ensured by using highly unsaturated phospholipids. There also did not seem to be any stability issues associated with a phase change according to the DSC analysis.

Figure 7:
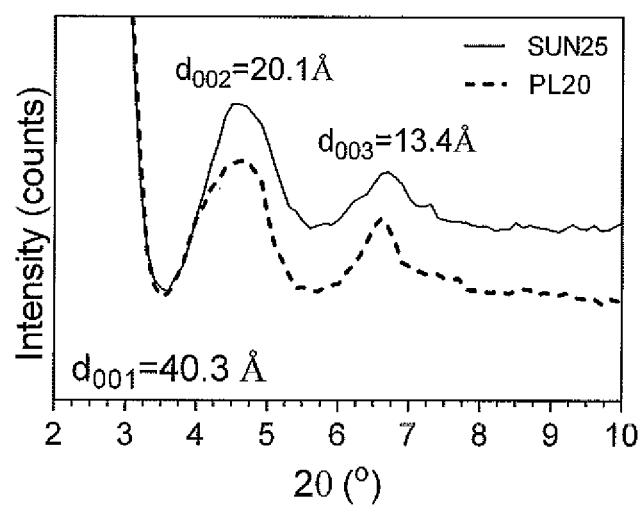
FIG. 7 illustrates powder X-ray diffraction patterns for spontaneously formed giant multilamellar vesicles prepared using soybean and sunflower lecithin.

An important structural aspect of vesicles is that they are bilayers in a lamellar phase. This so-called mesomorphic or polymorphic state/phase of self-assembly can be determined using small-angle powder X-ray diffraction (SAXS). X-ray scattering experiments were carried out using a Rigaku Multiflex Powder X-ray diffraction spectrometer (Rigaku, Tokyo, Japan). The copper X-ray tube (wavelength of 1.54 Å) was operated at 40 kV and 44 mA. The measurement scan rate was set at 0.1°/minute in the range 2θ=10-15° at 22° C. Peak positions were determined using MDI Jade 9 (MDI, Livermore, Calif., USA) software. The SAXS pattern obtained for the spontaneous GMVs is shown in FIG. 7. The relative spacing of the diffraction peaks was 1:2:3 in terms of the center position of the peaks, which is indicative of the existence of a lamellar phase (Zetzl et al. 2009).

Thus, these experiments confirm the spontaneous formation of giant multilamellar vesicles using commercial dry and deoiled lecithin.

Example 3. Preparation of LUVs from GMVs Using a Rotor-Stator

The thermal and shear stability of the spontaneous GMVs (sGMVs) was compared to that of 110 nm large unilamellar vesicles (LUV) prepared using a rotor-stator. The Magic Lab machine of IKA (IKAWorks, Inc., Wilmington, N.C., USA) was used to prepare the LUVs. The DR Dispatch reactor unit with 3 toolings in series, two very fine toolings with 3 shear zones per tooling, and one "centrifugal pump" tooling, was used. The sample has to flow through a narrow gap in between a stationary plate with holes (stator) and a rotating plate with holes (rotor). Fluid velocities can be very high in the openings and 26,000 RPM rotational speeds are possible. This machine functions under the same principle as an "Utra-Turrax" hand-held rotor-stator. As a matter of fact, one can use an "Ultra-Turrax" tooling with this machine if required.

Figure 8:
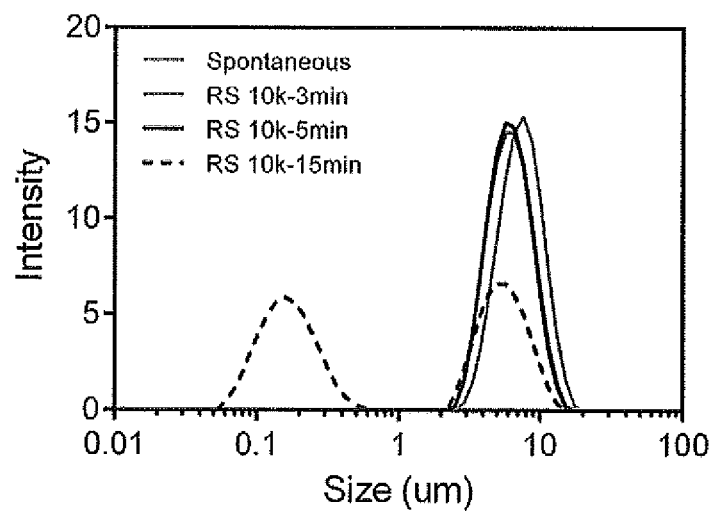
FIG. 8 graphically illustrates the size distribution of soy lecithin spontaneous giant multilamellar vesicles sheared in a rotor-stator for different periods of time.

First, the sensitivity of the spontaneous vesicles was monitored as a function of shear (FIG. 8). About 100 ml of soy lecithin sGMVs were sheared for 3, 5 and 15 minutes in the IKA rotor-stator mixing device at 10,000 RPM. By using this volume, the recirculation of the fluid was fast and the 100 mL were effectively continuously passed through the three toolings. Due to shear heating, it is important to keep the temperature of the sample below 80° C., which was achieved by flowing cold water through the rotor-stator assembly. The soy lecithin sGMV could withstand up to 5 minutes of shear at 10,000 RPM. Surprisingly, after 15 minutes, a large proportion of the 6.51 μm sGMVs had been reduced in size to ~160 nm. Intermediate sizes (between 6.5 μm and 160 nm) were not observed.

Figure 9:
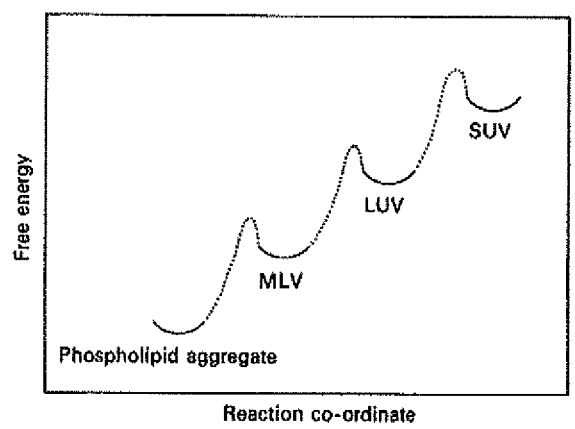
FIG. 9 illustrates the free energy reaction coordinate depicting the increasingly higher energy states of smaller vesicles.

This suggests that the spontaneous GMVs were occupying a well-defined quantized thermodynamic state. Energy input eventually results in taking the system out of equilibrium into a higher energy state, namely, the large unilamellar vesicle state shown in a free energy reaction coordinated diagram (FIG. 9). Small unilamellar vesicles (SUVs) could not be achieved with a rotor-stator regardless of the time or RPMs used. For this purpose, a higher energy input would be required, such as the one achievable using a microfluidizer, or other technique.

Figure 10:
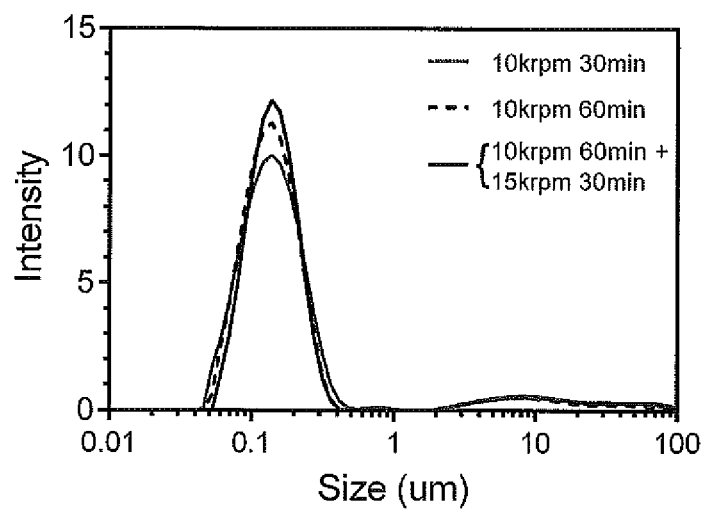
FIG. 10 graphically illustrates size distribution of sunflower lecithin large unilamellar vesicles sheared for different times at different shear rates.

Size reduction experiments were also conducted on 10% sunflower lecithin, Sunlec25, in 0.1M citrate buffer, pH 4.5. As shown in FIG. 10, 30 min of shearing in a rotor-stator at 10,000 RPM was sufficient for size reduction of sunflower lecithin into the ~100 nm range. Further shearing for 1 hour did not change the distribution.

Figure 11:
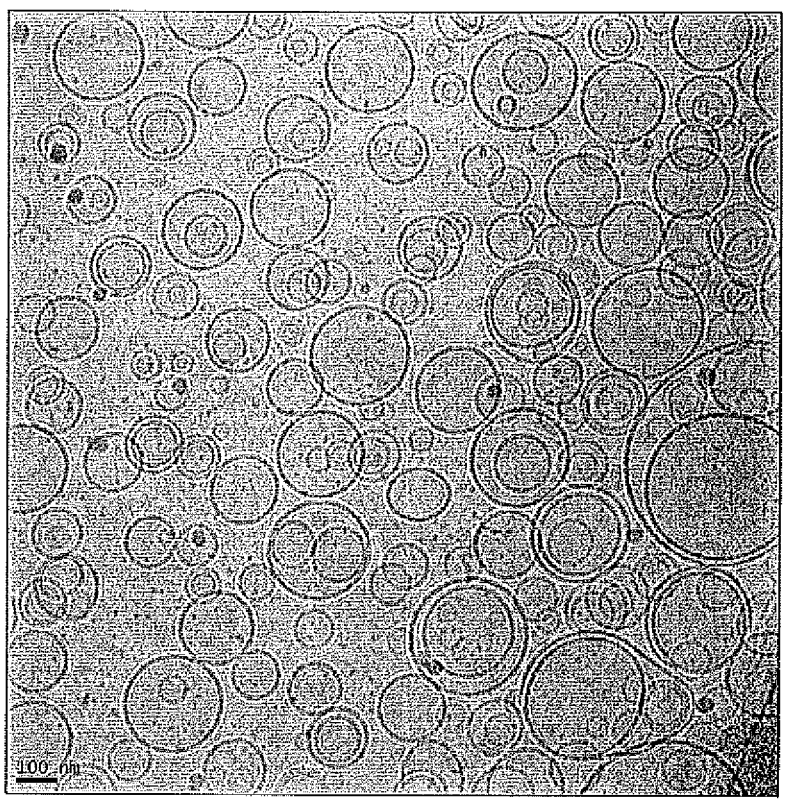
FIG. 11 illustrates cryogenic transmission electron microscopy of soybean lecithin large unilamellar vesicles.

The existence of LUVs was confirmed by cryogenic transmission electron microscopy. In preparation for imaging by cryo-TEM, 5 μl of sample were transferred onto a Quantifoil multi-hole grid which had been glow discharged. The suspension was then thinned by blotting with filter paper, and plunged into liquid ethane which was held close to liquid nitrogen temperature. The grid was stored in liquid nitrogen prior to being loaded into a pre-cooled holder which is inserted into a Tecnai TEM (Thermo Scientific, USA). Samples were viewed at −175° C. and 200 kV, and images were recorded using the Gatan 4K camera and the Gatan Digital Micrograph software (Gatan Inc., Roper Technologies, USA). FIG. 11 shows soy lecithin LUVs created using the rotosator. The single bilayer surrounding the vesicles and the average size of these can be appreciated from this micrograph. sGMVs were converted into LUVs using a rotor-stator. This is the first time such size reduction has been reported using a rotor-stator. Rotor-stators are used to make "pre-emulsions" and have never been listed as a viable method to make unilamellar vesicles. The average surface weighted diameters (D3,2) and standard deviations of the lecithin LUVs were determined by static light scattering measurements using a Mastersizer to be 115+/−3.12 nm for soybean PL20 and 116+/−1.41 nm for sunflower Sunlec25 lecithin.

Figure 12:
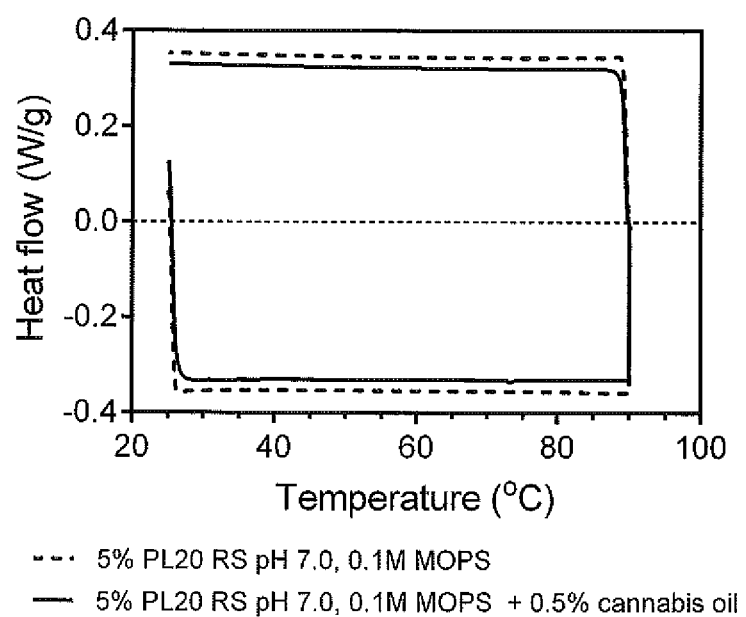
FIG. 12 are differential scanning calorimetric scans of soybean lecithin large unilamellar vesicles in 0.1M MOPS buffer, pH 7.2, both in heating (negative heat flows) and cooling (positive heat flows) modes.

The melting and cooling of the vesicles monitored by differential scanning calorimetry did not reveal any thermal phase transitions between freezing and 90° C. This is not surprising since the majority of the fatty acids of these lecithins are linoleic and linolenic acids, which have very low melting points (FIG. 12).

Example 5. Thermal Stability of sGMVs and LUVs

To use the present vesicles in foods/drinks, they would have to be pasteurized or sterilized. Thus, the thermal stability of the vesicles is important. To determine their thermal stability, two sets of experiments were conducted, one at 90° C. for 105 min and the second one at 60° C. for 160 hrs. Sealed glass containers of both vesicles preparations were placed in ovens at the two temperatures and following heating, the diameter of the vesicles were determined by static light scattering using a Mastersizer 2000.

Figure 13:
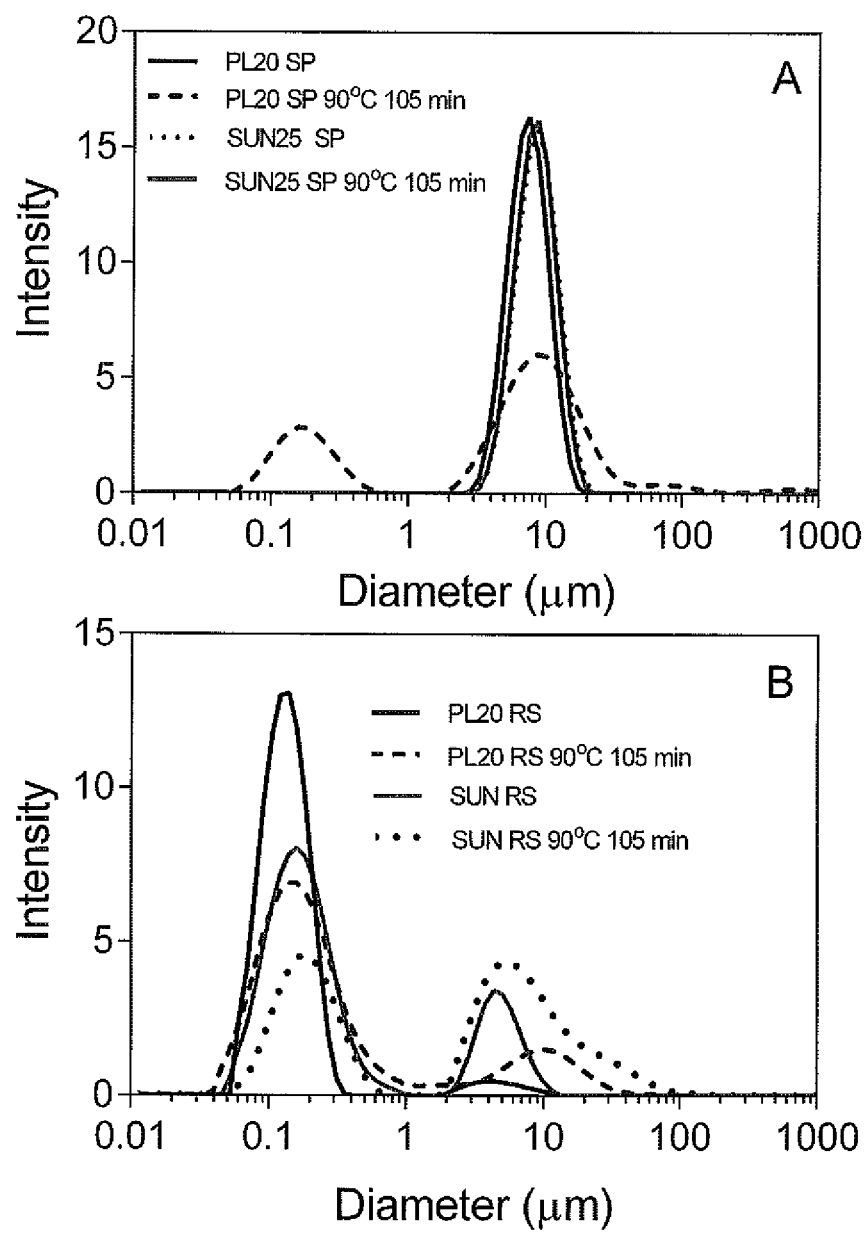
FIG. 13 graphically illustrates size distributions for soy and sunflower lecithin-derived spontaneous giant multilamellar vesicles (A) and large unilamellar vesicles (B) in 0.1M citrate buffer, pH 4.3, exposed to 90° C. for 105 min.

FIG. 13A clearly demonstrates how the average diameter of the sunflower lecithin sGMVs does not change during 1 hour and 45 minutes exposure to near boiling temperatures. However, exposure to high temperature caused a widening of the size distribution of soy lecithin vesicles and also resulted in the appearance of ~160 nm structures. It was not clear whether these were LUVs or some kind of micelle. Regardless, the soy lecithin showed a lower thermal stability than the sunflower lecithin, which may be a due to differences in molecular composition, namely higher PE contents and higher levels of the highly unsaturated linolenic acid.

FIG. 13B, on the other hand, shows the behavior of the corresponding LUV versions of these vesicles. For these experiments, samples were sheared in the IKA Magic Lab rotor-stator as described above for 1 min at 10,000 RPM and 4 min at 25,000 RPM at 30° C. Two interesting aspects of these systems were revealed. First, where the rotor-stator conditions were sufficient to yield a narrow size distribution for the PL20 soybean lecithin, they were not sufficient to fully convert all sGMVs into LUVs for Sunlec25 sunflower lecithin. This may be due to the soy lecithin sGMVs being less stable than the sunflower lecithin sGMVs, which resisted the transformation into LUVs. Upon exposure of these LUV preparations to the high heat conditions, both systems destabilized as evidenced by the appearance of a population of larger vesicles that may result from the combined effect of flocculation and coalescence. What is remarkable, though, is that the spontaneous sunflower GMVs were completely stable (FIG. 13A), where the corresponding sunflower LUVs were clearly not as stable (FIG. 13B). This provides support for the thermodynamic stability of sGMVs vs. the kinetic stability of LUVs.

The decreased stability of soy lecithin over sunflower lecithin could be due to the preference of certain polar lipids for specific mesomorphic phases. Tillock discussed this at length and a table from his 1986 paper is shown below (Tillock, 1986). One can immediately notice that phosphatidylethanolamine in isolation prefers to form Hex-II phases.

TABLE 3

Polymorphic phase preferences of liquid crystalline unsaturated lipids.
POLYMORPHIC PHASE PREFERENCES OF LIQUID CRYSTALLINE UNSATURATED LIPIDS

| Lipid | Phase preferences | |
|---|---|---|
| | Physiological conditions | Other conditions |
| Phosphatidylcholine | L | $H_{II}$ low hydration and high temp |
| Sphingomyelin | L | |
| Phosphatidylethanolamine | $H_{II}$ | L, pH ≥ 8.5 low temp |
| Phosphatidylserine | L | $H_{II}$, pH ≤ 3.5 |
| Phosphatidylglycerol | L | $H_{II}$, high temp, high salt conc. |
| Phosphatidylinositol | L | |
| Cardiolipin | L | $H_{II}$, divalent cations, pH ≤ 3, high salt |
| Phosphatidic acid | L | $H_{II}$, divalent cations, pH ≤ 3.5, high salt |
| Monoglucosyldiglyceride | $H_{II}$ | |
| Diglucosyldiglyceride | L | |
| Monogalactosyldiglyceride | $H_{II}$ | |
| Digalactosyldiglyceride | L | |
| Cerebroside | L | |
| Cerebroside sulfate | L | |
| Ganglioside | M | |
| Lysophosphatidylcholine | M | |
| Cholesterol | | Induces $H_{II}$ phase in mixed lipid systems |
| Unsaturated fatty acids | | Induce $H_{II}$ phase |

Note:
L, Lamellar; $H_{II}$, hexagonal; M, micellar.

Figure 14:
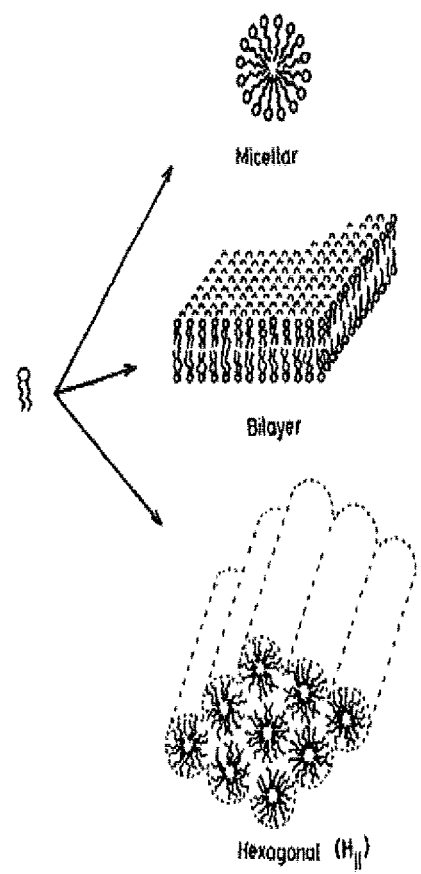
FIG. 14 illustrates polymorphic or mesomorphic preference of polar lipids and their associated overall molecular shape.

FIG. 14 illustrates mesomorphic structures in relationship to their overall molecular "shape" (Tillock, 1986; Cullis et al., 1986).

As set out in Table 2, soybean lecithin contains twice the amount of phosphatidylethanolamine (PE) than sunflower lecithin. This larger amount of PE could be responsible for the polymorphic/mesomorphic instability of soybean lecithin at high temperatures. The PC/PE ratio in soybean lecithin is 1, while the same ratio in sunflower lecithin it is 1.8. The relative amounts of PC vs. PE is much higher in sunflower lecithin due to a much lower PE content. A high PE content is associated with a greater tendency to form Hex-II structures, which may lead to vesicles destabilization. Soy lecithin is also more unsaturated than sunflower lecithin, which also induces lamellar-to-hexagonal II phase transformations. In general, increased unsaturation, increased temperature, decreases in headgroup size, decreases in headgroup ionization and decreases in water content all enhance the destabilization of lamellar phases into hexagonal-II phases, which leads to the formation of cylindrical micelles and vesicles breakdown.

Figure 15:
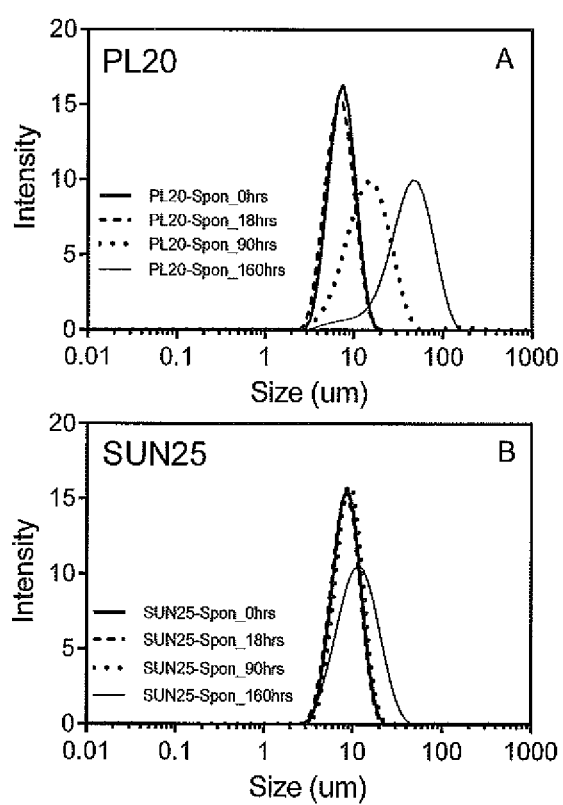
FIG. 15 graphically illustrates size distributions of (A) soybean and (B) sunflower spontaneous giant multilamellar vesicles heated at 60° C. for up to 7 days.
Figure 16:
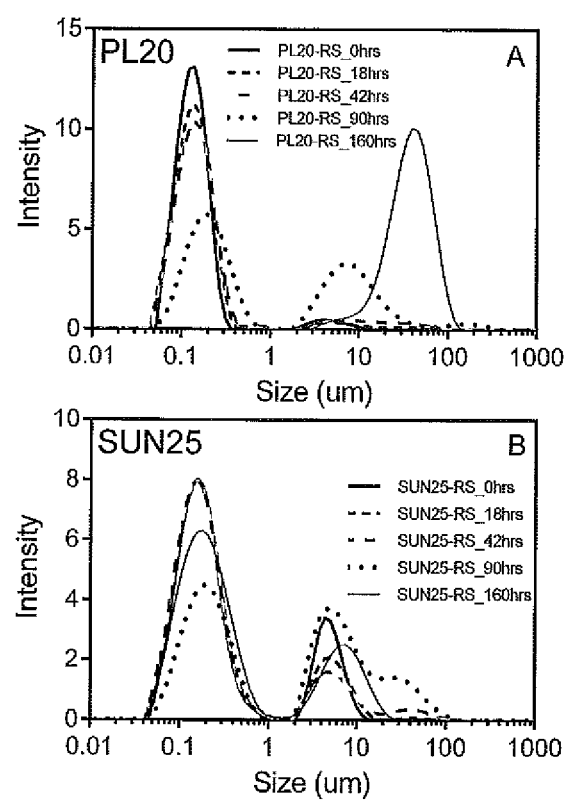
FIG. 16 graphically illustrates size distributions of (A) soybean and (B) sunflower large unilamellar vesicles heated at 60° C. for up to 7 days.
Figure 17:
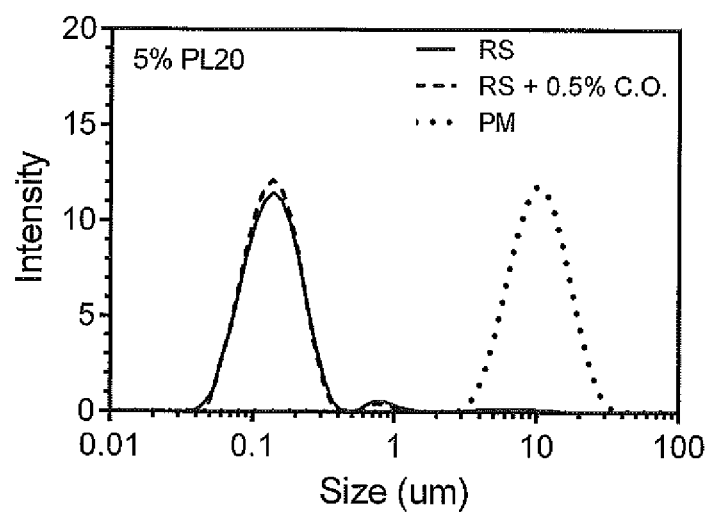
FIG. 17 graphically illustrates size distribution of soy lecithin large unilamellar vesicles containing cannabis oil.

The heat stability experiments were repeated at 60° C. FIG. 15 shows the behavior of the sGMVs while FIG. 17 shows the behavior of the LUVs. Again, sunflower sGMVs (FIG. 15A) were more stable than soybean sGMVs (FIG. 15B). Destabilization occurred after 90 h for soybean lecithin, 160 hrs for sunflower lecithin. For the LUVs, similar results were obtained, where soybean lecithin vesicles (FIG. 16A) destabilized before and to a greater extent than sunflower lecithin vesicles (FIG. 16B). These results suggest that higher amounts of monounsaturated fatty acids, such as oleic acid, provides increased oxidative stability, a greater tendency for vesicles to remain in the lamellar phase, as well as remaining in the liquid crystalline state (vs. gel state) over the temperature range 0-90° C.

Example 6. Manufacture, Characterization and Stability of Vesicles Containing Cannabis Oil Cannabis oil was then encapsulated within the phospholipid bilayers of both sGMVs and LUVs. Cannabis oil was first dissolved in 95% ethanol (0.5 g/ml) and then added slowly (1 drop every 3 seconds) into a 10% lecithin suspension at 60° C. This is an antisolvent technique in which the cannabis oil became insoluble in the new solvent medium and partitioned into the vesicles membranes since they are the only hydrophobic medium in the system. Cannabis oil in ethanol can be added to phospholipid at different stages, e.g. to a suspension of spontaneous GMVs, LUVs, or during the actual size reduction step in the rotor-stator.

Figure 18:
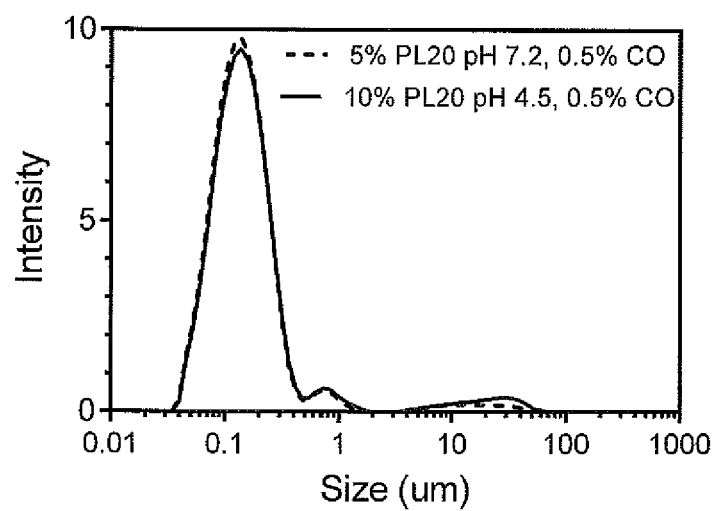
FIG. 18 graphically illustrates the size distribution of soy lecithin large unilamellar vesicles containing cannabis oil in either 0.1M MOPS pH 7.2 and 0.1M citrate pH 4.3.

The first experiment was carried out with soybean lecithin. A 5% (w/w) suspension of spontaneous GMVs was prepared at 60° C. using a paddle mixer. Specifically, a 10 g amount of Phospholipon 20 was added to a solution of 0.1M MOPS (3-(N-morpholino)propanesulfonic acid), pH 7.2 buffer. This mixture was paddle mixed at 300 RPM for 1 hour. The lecithin was fully dissolved in this period. A 100 mL aliquot of this sample was then transferred to the IKA Magic Lab machine. The temperature was maintained between 60 and 70° C. by water recirculation. Temperatures above 80° C. proved deleterious to LUV manufacture and phase separation sometimes occurred. The sample was then sheared at 20,000 RPM for 30 minutes. One milliliter of the 0.5 g/ml cannabis oil in ethanol solution was slowly dripped into the vortex of the IKA Magic Lab rotor-stator while the machine was running. The results from this experiment are shown in FIG. 17. The figure illustrates the step-function like decrease in size from sGMVs to LUVs and the fact that incorporation of cannabinoids did not change this distribution. The stability of these vesicles was monitored for over two months and the size distribution did not change (FIG. 18). Moreover, vesicles formed using 10% soy lecithin in 0.1M sodium citrate pH 4.5 also did not have an impact on physical stability of the LUVs (FIG. 18). However, the pH must be greater than the pK of the phosphate group of the phospholipid to avoid its protonation which would adversely affect lipsome stability. Conducting the cannabis incorporation at pH 4.5 advantageously represents a hurdle or barrier to microbial growth and thus constitutes a better system for the commercial production of encapsulated cannabis oil. In addition, since the procedure was carried out at 60-70° C. for over half an hour, the material has effectively also been pasteurized.

Encapsulation, as above, was conducted using 50% phosphatidylcholine lecithin, mainly Sunlipon50. Addition of cannabis oil to 10% sunflower lecithin LUVs in 0.1M citrate buffer pH 4.5 resulted in coagulation and separation of a brown precipitate at 0.5% cannabis oil levels. Thus, lecithin of less than 50% phosphatidylcholine is preferable.

Encapsulation studies of cannabis oil in both sGMVs and LUVs were then conducted using soybean and sunflower lecithin. 10% w/w liposomal suspensions were prepared as described above in 0.1M sodium citrate pH 4.5 comprising entrapped/encapsulated cannabis oil dissolved in 95% ethanol. These samples had a final added concentration of 5, 10, 15 and 20 mg/mL cannabis oil for 100 mg/mL of lecithin.

After encapsulation, samples were centrifuged at 4000 rpm for 10 minutes at room temperature in order to remove any cannabinoids not bound specifically to the vesicles. An aliquot of the supernatant of the labelled liposomal preparations was then extracted using the Bligh and Dyer method (Canadian Journal of Biochemistry and Physiology. 1959. 37: 911-917). The lower chloroform layer of the extract contained the lipid-soluble components, namely the cannabinoids. The composition of this extract was determined using gas-liquid chromatography. An Agilent 6890-series gas chromatograph (Agilent Technologies, Inc., Wilmington, Del., USA) with a 7683-series auto-sampler was used to determine the amount of cannabinoid in the samples. A 15 m×0.25 mm internal diameter fused silica column with a 0.20 µm DB5 film thickness was used (Agilent Inc., USA). The oven temperature was maintained at 80° C. for 5 minutes and then programmed to increase from 80 to 300° C. at 12° C./min. The injector temperature was set at 250° C., and was operated at 19.2 psi with a hydrogen flow rate of 85 mL/min. Split ratio was set at 10:1. Helium, the carrier gas, flowed at an average velocity of 25 cm/s. A flame ionization detector was set at 350° C. with 450 mL/min air and 50 mL/min helium flowing. The separated peaks were analyzed using Open LAB software (Agilent Technologies). The amount of cannabinoid was determined by comparing retention times of the peaks to an internal standard.

Figure 19:
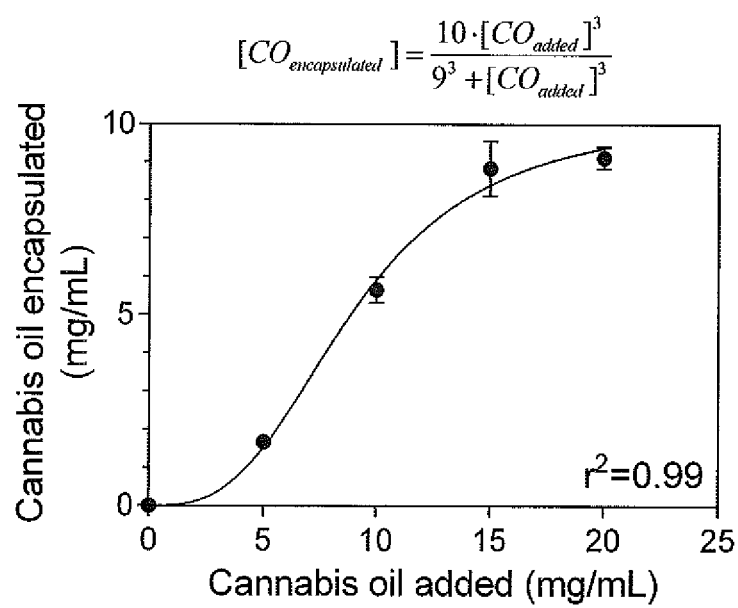
FIG. 19 graphically illustrates encapsulation efficiency of cannabis oil in LUVs prepared from 10% sunflower lecithin in 0.1M citrate buffer, pH 4.3. The fit shown is for specific cooperative binding reaching saturation.

Results are shown in FIG. 19. The results demonstrate that the ~100 nm LUVs do not inherently have the capacity to incorporate high levels of cannabis oil within their structure. This is possibly due to the higher curvature of within these 'smaller' vesicles, which would put strain on the bilayer if cannabinoids become incorporated at high levels. A specific and cooperative saturation binding model fit the data, which suggests that the cannabinoids were partitioning into the membranes and binding specifically to the phospholipids in the bilayer. The cooperative effect could indicate that the bilayer needs to rearrange to welcome cannabinoids within its structure. Once the membrane is "primed", it can then uptake more cannabinoid. The model also indicates a maximal loading capacity of 10 mg/mL for this 10% sunflower lecithin composition structured as LUVs of approximately 100 nm in diameter. This constitutes about 50% encapsulation efficiency for the LUVs.

Figure 20:
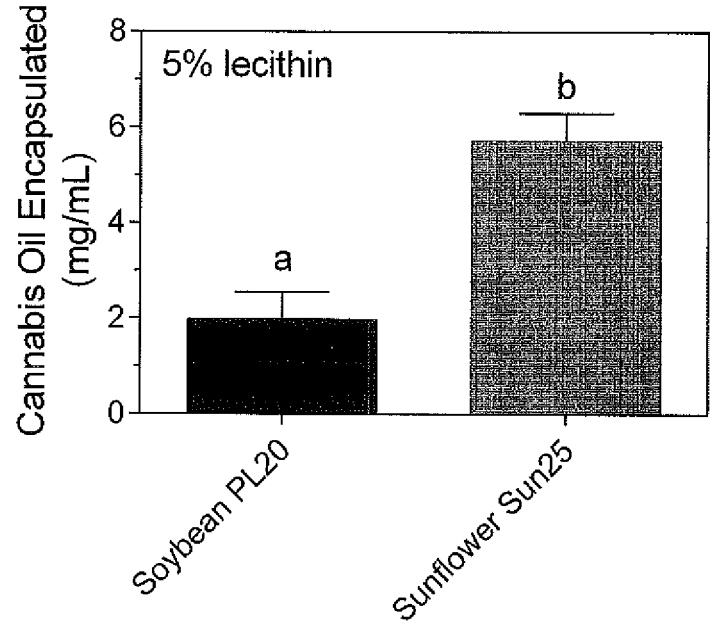
FIG. 20 graphically illustrates encapsulation of cannabis oil in LUVs prepared from soybean and sunflower lecithin in 0.1M citrate buffer, pH 4.3.

FIG. 20 illustrates that sunflower lecithin is much more efficient in encapsulating cannabis oil than soybean lecithin. Encapsulation efficiency of cannabinoid in sunflower lecithin was ~50-60%, while the soybean lecithin LUVs exhibited a ~3× lower encapsulation efficiency than the sunflower lecithin. These results also suggest that incorporation of cannabis oil into sunflower lecithin LUVs is more efficient than in soybean lecithin LUVs. The 50 mg of lecithin present in 1 mL of suspension can easily trap 5-6 mg of cannabis oil. This 1:10 w/w (cannabis oil to lecithin) ratio translates to a 1:4 mol/mol ratio.

Figure 21:
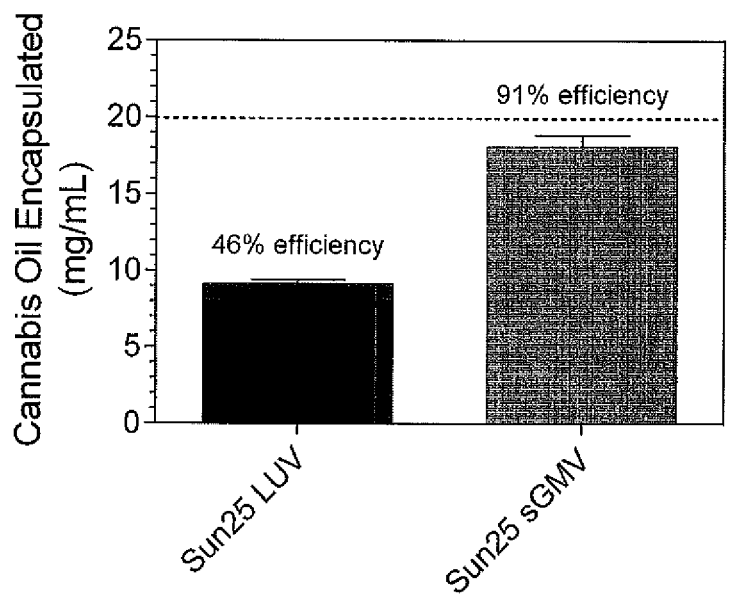
FIG. 21 graphically illustrates encapsulation of cannabis oil in LUVs and sGMVs prepared using 10% sunflower lecithin. Cannabis oil was added at 20 mg/mL levels to the dispersion in 0.1M citrate buffer at pH 4.3.

The experiment was repeated comparing LUVs with sGMVs. The results are shown in FIG. 21. Encapsulation efficiency of the sGMVs prepared form 10% sunflower lecithin was almost 90%, while in contrast the efficiency for LUVs prepared using the same 10% sunflower lecithin was about half of that. Thus, for the sGMVs containing 100 mg of lecithin per ml, 18.1 mg of cannabis oil could be encapsulated per ml, which translates to 1:2.3 mol/mol cannabis oil:lecithin ratio.

These results indicate that it is possible to prepare 10% sGMV phospholipid dispersions containing close to 20 mg/mL cannabis oil, without any loss of the valuable product. The data further indicates that it is also possible to make LUV phospholipid dispersions with 50% encapsulation efficiency. Obviously the smaller vesicles would yield a more translucent sample upon dilution, while with sGMV higher loadings more turbid solutions would be obtained.

Example 7. Antioxidant Activity of Cannabis Oil in Vesicles Combined with Antioxidants One of the greatest problems with the use of cannabis oil is the oxidation of the active component, tetrahydrocannabinol (THC), to cannabinol (CBN); however, it is noted that THC and CBN should have antioxidant activity due to the phenolic ring(s) they contain.

To investigate this, accelerated oxidation tests of cannabis oil in the labile soybean oil with and without additional antioxidants were conducted. The Rancimat (Metrohm MG, Herisau, Switzerland) test was used for this purpose as follows. 2 g of oil were placed in a narrow glass flask, heated to 110° C. and air was bubbled through the oil at 20 ml/min. This caused accelerated oxidation. As the liquid oxidized, volatile secondary oxidation products were volatilized and bubbled into room temperature water. This caused them to dissolve in the water, which results in an increase in its electrical conductivity. The conductivity is measured continuously using a standard electrode. It is noted that the oxidation flasks were cleaned with an industrial degreaser since results are significantly affected by any contamination within the flasks. Results are shown in Table 5.

TABLE 5

Induction times of oxidation determined using the Rancimat method at 110° C.

| Sample | Rancimat Induction time (hr) | Induction time extension (hr) |
|---|---|---|
| Soybean Oil (SBO) | 8.2, 8.3, 7.8[a] | 0 |
| SBO + 0.1% water | 5.8 | −2 |
| SBO + 0.01% TBHQ | 15.3[b] | 7.1 |
| SBO + 0.02% TBHQ | 22.5 | 14.3 |
| SBO + 0.04% TBHQ | 36.7 | 28.5 |
| SBO + 0.5% SUN25 | 11.9 | 4.1 |
| SBO + 0.5% SUN25 + 0.01% TBHQ | 27.6 | 19.8 |
| SBO + 0.5% PL20 | 19.8 | 12 |
| SBO + 0.5% PL20 + 0.01% TBHQ | 28.4 | 20.6 |
| SBO + 2.5 mg/g *cannabis* oil | 8.5 | 0.7 |
| SBO + 4.8 mg/g *cannabis* oil | 10.1 | 2.3 |
| SBO + 8.0 mg/g *cannabis* oil | 11.3 | 3.5 |
| SBO + 4.8 mg/g *cannabis* oil + 0.01% TBHQ | 15.7 | 7.9 |
| SBO + 4.8 mg/g *cannabis* oil + 0.5% SUN25 | 17.4 | 9.6 |
| SBO + 4.8 mg/g *cannabis* oil + 0.5% SUN25 + 0.01% TBHQ | 28.8 | 21 |
| SBO + 4.8 mg/g *cannabis* oil + 0.5% PL20 | 25.2 | 17 |
| SBO + 4.8 mg/g *cannabis* oil + 0.5% PL20 + 0.01% TBHQ | 32.1 | 23.9 |

[a]Different sources of soybean oil displayed different sensitivities towards oxidation. The soybean oil used for these experiment had an induction time of 7.8 hours.
[b]These three experiments of THBQ addition to SBO were carried out with soybean oil with an induction time of 8.2 hours As shown in Table 5, the induction time for Rancimat oxidation of soybean oil was ~8 hours. This value was highly reproducible across three different types of soybean oil. Interestingly, addition of just 0.1% water decreases the oxidative stability of the oil significantly by two hours, probably due to hydrolysis of the triglycerides to fatty acids, which then can volatilize and/or oxidize. As a positive control, increasing levels of the most powerful synthetic phenolic antioxidant, TBHQ (tert-butylhydroquinone). The usual usage level of TBHQ is 0.01% (w/w), which is equivalent to 100 ppm, and this provides a shelf life to most vegetable oils of one year at ~25° C. For every 100 ppm TBHQ added to the oils, the induction time of oxidation increased by 7.1-7.2 hours, in a linear fashion ($t_i$=8.12+ 0.07154 [ppm TBHQ], $r^2$=0.99).

It was then determined whether or not cannabis oil had antioxidant activity. Addition of cannabis oil to soybean oil at a level of 8 mg/g of oil displayed antioxidant behavior and increased the induction time of oxidation of the soybean oil by 3.5 hours at 110° C. To clarify, this means that cannabis oil will oxidize preferentially over soybean oil, thus protecting soybean oil from oxidation. Addition of 0.01% TBHQ to soybean oil containing 4.8 mg/g cannabis oil increased the induction time of oxidation from 7.8 hours to 15.7 hours. This is consistent with a simple linear addition of the respective induction times of oxidation for the different components. No interaction between the TBHQ and the cannabinoids was observed, and the cannabis oil did not oxidize during this period since an induction time of 18 hours was not attained.

The antioxidant activity of the deoiled and dried lecithins (soybean and sunflower lecithin) was determined. These were added to soybean oil. Unexpectedly, both soybean and sunflower lecithins displayed strong antioxidant potential at 0.5% addition levels, extending the induction time of oxidation from 7.8 hours to 11.9 hours for Sunlec25 and to 19.8 hours for PL20. Please note that at 5 mg/g addition, the concentration is 50 times higher than TBHQ, but in the range of cannabis oil. Since lecithin is not usually considered an antioxidant, this finding was surprising. It also means that encapsulation of cannabis oil within lecithin could protect the active components in cannabis oil, particularly THC against oxidation.

The effects of 0.01% TBHQ addition to soybean oil with 0.5% lecithin was then determined. Again, surprisingly, this combination was found to increase induction times from 11.9 to 27.6 hours for sunflower lecithin and from 19.8 to 28.4 hours for soybean lecithin. Addition of TBHQ to soybean oil alone increased the induction time by 7.1 hours only, but in combination with lecithin, induction time was increased an additional 15.7 hours and 17.4 hours for sunflower and soybean lecithin, respectively. This massive increase in induction time can only be interpreted as a strong synergistic effect between lecithin and phenolic antioxidants such as TBHQ.

Addition of both lecithin and cannabis oil to the soybean oil also increased the induction time of oxidation at 110° C. Addition of 4.8 mg/g of cannabis oil to soybean oil with 0.5% sunflower lecithin increased the induction time to 17.4 hours, a 5.5 hour increase over SBO+0.5% sunflower lecithin. Recall that the addition of 4.8 mg/g of cannabis oil to soybean oil increased the induction time by 2.3 hours, so this result also suggests a synergism between sunflower lecithin and cannabis oil.

A further combination of 0.01% TBHQ to the soybean oil+lecithin+cannabis oil mixtures was also conducted, and induction time of oxidation was measured. The addition of 0.01% TBHQ to soybean oil containing 0.5% sunflower lecithin and 4.8 mg/g cannabis oil was determined to be 28.8 hours. Recall that addition of 0.01% TBHQ to soybean oil increased the induction time by 7.1 hours, the addition of sunflower lecithin increases it by 4.1 hours, and the addition of cannabis oil by 2.3 hours. The additive time on top of an induction time of oxidation for soybean oil of 7.8 hours should then be 21.7 hours. Thus, the 28.8 hours actually attained exhibits an additional 7.1 hours of stabilization. This is very significant and points to a synergistic effect between TBHQ, cannabinoids and lecithin. Similar effects were observed for TBHQ addition to soybean oil+soybean lecithin+cannabis oil.

These results are significant since they point to the added stability benefits of incorporating cannabis oil within phospholipid vesicles. Not only are they now encapsulated within a hydrophobic environment, but the environment protects the active components within the cannabis oil against oxidation, thus retaining the full dosage for commercially relevant periods of time. Additionally, cannabinoids interact synergistically with phenolic antioxidants such as tert-butyl hydroxy quinone (TBHQ), butylated hydroxy toluene (BHT), butylated hydroxyl anisole (BHA), propyl gallate (PG) and tocopherols. Addition of these to the liposomal matrix will only enhance the stability of cannabinoids further.

To confirm which of the contents are protected from oxidation, the molecular makeup of the oxidized product was analyzed. Five 1 ml chromatography glass vials were used for this purpose. 14 mg of cannabis oil were delivered into the vials from an ethanolic solution and the weight checked after evaporation of the solvent. Stock solutions of 0.5% sunflower lecithin (Sunlec25), 0.01% TBHQ and 0.5% lecithin+0.01% TBHQ were prepared. The following samples were then prepared:

A: 14 mg cannabis oil
B: 14 mg of cannabis oil+1 ml of 0.5% sunflower lecithin
C: 14 mg of cannabis oil+1 ml of 0.01% TBHQ
D: 14 mg of cannabis oil+1 ml of 0.5% sunflower lecithin+ 0.01% TBHQ
E: 14 mg cannabis oil The chloroform was evaporated under a stream of air until completely dry. The dry films of Samples A-D were heated for 1.5 hours at 100° C., while sample E remained at room temperature. After the heating period, samples were removed from the oven, allowed to cool to room temperature and then 1 ml of fresh chloroform was added to each vial and capped. Samples were then analyzed by gas-liquid chromatography as described previously. An Agilent 6890-series gas chromatograph (Agilent Technologies, Inc., Wilmington, Del., USA) with a 7683-series auto-sampler was used to determine the amount of X in the samples. A 15 m×0.25 mm internal diameter fused silica column with a 0.20 µm DB5 film thickness was used (Agilent Inc., USA). The oven temperature was maintained at 80° C. for 5 minutes and then programmed to increase from 80 to 300° C. at 12° C./min. The injector temperature was set at 250° C., and was operated at 19.2 psi with a hydrogen flow rate of 85 mL/min. Split ratio was set at 10:1. Helium, the carrier gas, flowed at an average velocity of 25 cm/s. A flame ionization detector was set at 350° C. with 450 mL/min air and 50 mL/min helium flowing. The separated peaks were analyzed using Open LAB software (Agilent Technologies). The amount of cannabinoid was determined by comparing retention times of the peaks to an internal standard. For this analysis, the main THC peak was analyzed.

Figure 22:
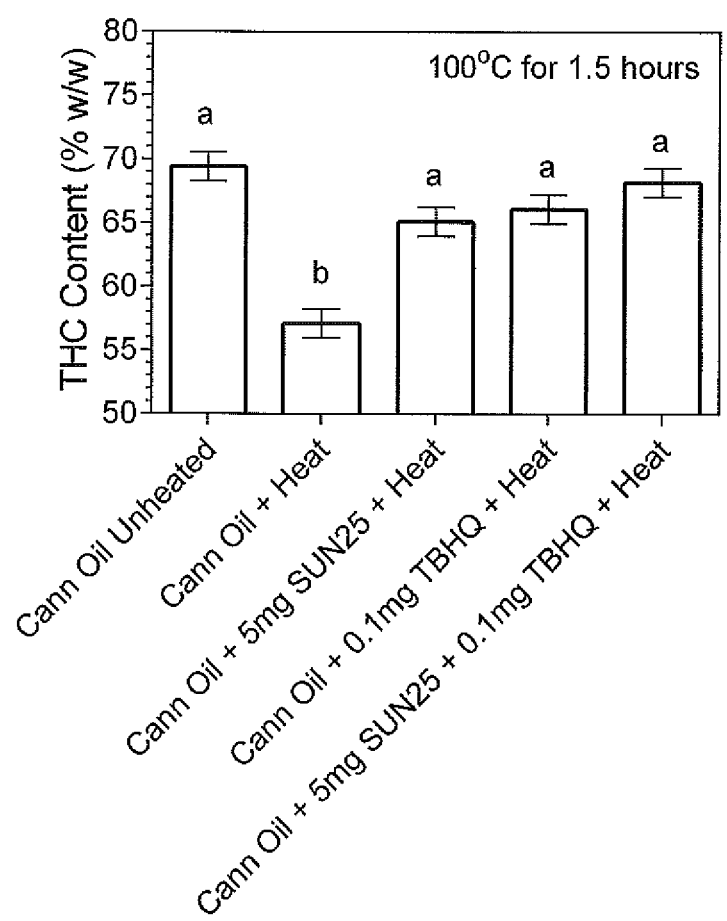
FIG. 22 graphically illustrates changes in THC relative proportion upon heating to 100° C. for 1.5 hours. Values represent means and standard deviations of two replicates. Bars with the same letter are not significantly different (P>0.05).

Results from this analysis are shown in FIG. 22. As can be seen, heating caused a significant degradation of THC, which was prevented by lecithin, the TBHQ and the mixture of lecithin and TBHQ. There were no differences between the antioxidant treatments in terms of preservation of THC integrity under these accelerated test conditions. This example proves that lecithin, THBQ and their mixture are acting as primary antioxidants for cannabinoids.

Example 8. Atomic Scale Molecular Mechanics Computer Simulation for the Comparison of the Cholesterol and Cannabinol A comparison of cannabinol and cholesterol was conducted to confirm the suitability of the present vesicles for loading with different cargo.

For these atomistic simulations, three programs were used, ChemSite Pro version 10.5 (Copyright David Michael, Ph.D), Molecular Modelling Pro Plus (MMP+) version 8.1.40 (Norgwyn Montgomery Software Inc, James A. Quinn, lead programmer), and ChemElectrica version 3.2.12 (Norgwyn Montgomery Software Inc, James A. Quinn, lead programmer).

The structure file for cholesterol were found in ChemSite under "Lipids" while the structure file for cannabinol was found in ChemElectrica under "Narcotics". The structures were saved in a mol format and opened in MMP+. The geometry of the structures was then optimized within MMP+using Allinger's "Standard MM2" protocol for finding the minimum energy for the structure ("Geometry Minimize"). Once the geometries were minimized, two analyses were carried out. The first was to "Calculate Dimensions" of the two molecules and the second analysis was to "Calculate Solubility Parameters". The melting points used for Cholesterol and Cannabinol were 148° C. and 77° C., respectively. A comparison of the structural characteristics of the two molecules is shown in Table 1 and the final optimized geometries in FIG. 1.

TABLE 1

Structural and chemical properties of cholesterol and cannabinol

| Molecular Characteristic | Cholesterol | Cannabinol |
|---|---|---|
| Maximum length along x-axis (Å) | 19.9 | 17.4 |
| Maximum width above x-axis (Å) | 4.37 | 4.02 |
| Maximum width below x-axis (Å) | −4.45 | −5.72 |
| Depth in front of x-axis (Å) | 3.78 | 3.66 |
| Depth behind x-axis (Å) | −3.95 | −3.70 |
| Maximum width (perpendicular to x-axis, drawn along y-axis, Å) | 8.82 | 9.77 |
| Minimum width (any direction Perpendicular to x-axis, Å) | 7.64 | 6.48 |
| Hoy's 3-D Solubility Parameters ($J^{1/2}$ cm$^{-3/2}$) | | |
| Molar attraction function | 18.22 | 19.94 |
| Dispersion | 15.88 | 15.32 |
| Polarity | 6.39 | 8.64 |
| Hydrogen bonding | 6.24 | 9.40 |
| Molecular aggregation number | 1.13 | 1.28 |
| Energy of cohesion | 118204 | 104521 |
| Molar volume | 385.65 | 289.90 |

A cursory look at Table 1 reveals some striking similarities between the molecules. Indicated in the gray highlights are the depths (the thickness) of the molecules. These two molecules are "flat" due to their extended ring geometry and have thus one relatively long dimension, the length, an intermediate dimension, the width, and a small dimension, the depth.

However, structure/geometry is not the only consideration when comparing the partitioning behavior of these molecules into a phospholipid bilayer. Their chemical properties, in terms of solubility, should be similar as well. For this purpose, Hoy Solubility Parameters, a more theoretical version of the Hansen Solubility Parameters (Hoy, 1989) was used. Results are also shown in Table 1. Of note is the similarity in the Dispersion component of the Hoy Solubility Parameter. The environment within the fatty acid chains of a phospholipid bilayer is very nonpolar and thus its chemical properties are governed mainly by London dispersion forces. This analysis shows that both cholesterol and cannabinol have inherently similar nonpolar characteristics, which should equate to similar partitioning behaviors, or solubility, within the fatty acid chains of a phospholipid bilayer. Many of the other solubility parameters are similar as well.

This analysis confirms the uptake of molecules that exhibit appropriate structural features, i.e., size characteristics in specific directions, and phospholipid bilayer partitioning and solubility behavior, related to the relative balance between polar and dispersion forces, may be effectively encapsulated at high concentration by the present GMVs and LUVs. Preferred cargo molecular features for encapsulation purposes include, size features such as 15-20 Angstroms in length, 6-10 Angstroms in width and 3-4 Angstroms in depth (e.g. a flat molecule). The molecule must be capable of phospholipid bilayer partitioning, having a length that is no longer than the fatty acid chains on the phospholipid a width to permit fitting between fatty acid chains. Preferred dispersion solubility is about 14-16 $J^{1/2}$ $cm^{-3/2}$ and hydrogen bonding and polarity solubility of about 6-10 $J^{1/2}$ $cm^{3/2}$.

REFERENCES

Allen, T. M. and Cullis, P. R. 2013. Liposomal drug delivery systems: from concept to clinical applications. Advanced drug delivery reviews 65: 36-48

Bangham, A. and Home, R. W. 1964. Negative staining of phospholipids and their structural modification by surface-active agents as observed in the electron microscope. J. Molecular Biology 8: 660-668

Bligh, E. G. and Dyer, W. J. 1959. A rapid method of total lipid extraction and purification. Canadian Journal of Biochemistry and Physiology 37: 911-917

Bozzuto, G. and Molinari, A. 2015. Liposomes as nano-medical devices. International Journal of Nanomedicine 10: 975-999

Cullis, P. R., Hope, M. J. and Tilcock, C. P. S. 1986. Lipid polymorphism and the roles of lipids in membranes. Chemistry and Physics of Lipids 40: 127-144

Demel, R. A., Jansen, J. W. C. M., van Dijck, P. W. M. and van Deenen, L. L. M. 1977. The preferential interactions of cholesterol with different classes of phospholipids. Biochimica et Biophysica Acta 465: 1-10

Epand, R. M., Bach, D., and Wachel, E. 2016. In vitro determination of the solubility limit of cholesterol in phospholipid bilayers. Chemistry and Physics of Lipids 199: 3-10

Frolov, V., Shnyrova, A. V. and Zimmerberg, J. 2011. Lipid Polymorphisms and Membrane Shape. Cold Spring Harbor Perspectives in Biology 3:a004747 Goldfine, H. 1984. Bacterial membranes and lipid packing theory. Journal of Lipid Research 25: 1501-507

Guida, V. 2010. Thermodynamics and kinetics of vesicles formation process. Advances in Colloid and Interface Science 161: 77-88

Helfrich, W. 1973. Elastic properties of lipid bilayers: theory and possible experiments. Z. Naturforschung 28 c: 693-703.

Hope, M. J., Bally, M. B., Mayer, L. D., Janoff, A. S. and Cullis, P. R. 1986. Generation of multilamellar and uni-lamellar phospholipid vesicles. Chemistry and Physics of Lipids 40: 89-107

Hoy, K. L. 1989. Solubility Parameter as a Design Parameter for Water Borne Polymers and Coatings. Journal of Coated Fabrics 19:53-67

Israelachvilli, J. 1992. Intermolecular & Surface Forces. Academic Press, N.Y. pp 450.

Lasic, D. D. 1988a. The mechanism of vesicle formation. Biochemical Journal 259:1-11

Lasic, D. D. 1988b. On the thermodynamic stability of liposomes. Journal of Colloid and Interface Science 140: 302-304

Olson, F., Hunt, C. A., Szoka, F. C., Vail, W. J. and Papahadjopoulos, D. 1979. Preparation of liposomes of defined size distribution by extrusion through polycarbonate membranes. Biochimica and Biophysica Acta 557: 9-23

Safran, S. A., Pincus, P., and Andelman, D. 1990. Theory of spontaneous vesicle formation in surfactant mixtures. Science 248: 354-356

Safran, S. A., Pincus, P., and Andelman, D. and MacKintosh, F. C. 1991. Stability and phase behavior or mixed surfactant vesicles. Physical Review A 43: 1071-1078.

Tillock, C. P. S. 1986. Lipid polymorphism. Chemistry and Physics of Lipids 40: 109-125 van Dijck, P. W. M, de Druijff, B., van Decnen, L. L. M., de Gier, J and Demel, R. A. 1976. The preference of cholesterol for phosphatidylcholine in mixed phospatidylcholine-phosphatidylethanolamine bilayers. Biochimica Biophysica Acta 455: 576-587

Wattenberg, B. W. and Silbert, D. F. 1983. Sterol partitioning among intracellular membranes. J. Biological Chemistry 258: 2284-2289

Wang, F. C., Acevedo, N. C., Marangoni, A. G. 2017. Food and Function 8: 3964-3969

Woodle, M. C. and Paphadjopoulos, D. 1989. Liposome preparation and size characterization. Methods in Enzymology 171: 193-217

Zetzl, A., Ollivon, M., Marangoni, A. 2009. A coupled differential scanning calorimetry and X-ray study of the mesomorphic phases of monostearin and stearic acid in water. Crystal Growth and Design 9: 3928-3933

The invention claimed is:

1. Giant multi-lamellar vesicles in the size range of 3-10 μm which consist of deoiled lecithin, wherein the lecithin comprises phosphatidylcholines in an amount in the range of about 15-50% by wt, phosphatidylethanolamines in an amount in the range of about 5-25 wt % and phosphatidic acids in an amount of less than 10% by wt.

2. The vesicles of claim 1, wherein the lecithin comprises a phosphatidylcholine to phosphatidyletanolamine (PC:PE) ratio of in the range of about 1:1 to 5:1 PC:PE.

3. The vesicles of claim 1, wherein the lecithin comprises a PC:PE molar or mass ratio of greater than 1.

4. The vesicles of claim 1, wherein the lecithin comprises about 5-15% by wt phosphatidylethanolamines.

5. The vesicles of claim 1, which are in a liquid crystalline state over the temperature range 0-90° C.

6. The vesicles of claim 1, prepared by mixing the lecithin in a buffer until fully dispersed.

7. The vesicles of claim 6, wherein lecithin in an amount of about 2-20% by wt is mixed with the buffer.

8. The vesicles of claim 6, wherein the buffer is an acidic buffer.

9. The vesicles of claim 7, wherein lecithin in an amount of 10% (w/w) is mixed with buffer at a pH that is equal to or greater than the effective pK of the phosphate group of the phospholipid mixture in the lecithin.

10. The vesicles of claim 1, comprising encapsulated cargo.

11. The vesicles of claim 10, comprising a cargo to lecithin ratio of at least 1:5 mol:mol.

12. The vesicles of claim 10, wherein the cargo comprises a cannabinoid.

13. The vesicles of claim 12, wherein the cannabinoid is selected from the group consisting of: cannabidiol (CBD), cannabinol (CBN), cannabichromene (CBC), cannabichromenic acid (CBCA), cannabidiolic acid (CBDA), cannabidivarin (CBDV), cannabigerol (CBG), cannabigerolic acid (CBGA), cannabigerivarin (CBGV), cannabidivarin acid (CBDVA), cannabinovarin (CBNV), cannabinodiol (CBDL), cannabicyclol (CBL), cannabielsoin (CBE), cannabitriol (CBT), cannabivarin (CBV), cannabichromevarin (CBCV), cannabigerol monoethyl ether (CBGM), tetrahydrocannabinols (THC), tetrahydrocannabivarin (THCV), naphthoylindoles; phenylacetylindoles; benzoylindoles; cyclohexylphenoles; and HU-210.

14. The vesicles of claim 10, wherein the cargo comprises a terpene.

15. The vesicles of claim 13, additionally comprising an antioxidant.

16. The vesicles of claim 15, wherein the antioxidant is a phenolic antioxidant.

17. The vesicles of claim 16, wherein the phenolic antioxidant is tert-butyl hydroxy quinone (TBHQ), butylated hydroxy toluene (BHT), butylated hydroxyl anisole (BHA), propyl gallate (PG), a tocopherol or a mixture thereof.

18. The vesicles of claim 10, prepared by dissolving the cargo in a solvent and mixing with preformed giant multi-lamellar vesicles having a size of at least 3 μm for a time sufficient for uptake of the cargo.

19. A method of preparing the vesicles of claim 1, comprising mixing the deoiled lecithin in an aqueous buffer until fully dispersed.

20. The method of claim 19, wherein the pH of the buffer is between about 2.5-5 and the method is conducted at a temperature in the range of between 55-75° C.

21. A method of preparing large unilamellar vesicles (LUVs) having a size in the range of about 100-400 nm comprising the step of exposing giant multi-lamellar vesicles (GMVs) as defined in claim 1 to mixing in range of about 10000-30000 rpm, optionally with a rotor-stator, for a period of time sufficient to form the LUVs.

22. The method of claim 21, wherein the GMVs are mixed with a rotor-stator.

23. The method of claim 21, wherein cargo is dissolved in a solvent and combined with i) the giant multi-lamellar vesicles, or ii) LUVs, followed by mixing to form cargo-containing vesicles.

24. The method of claim 14, wherein the terpene is selected from the group consisting of myrcene, beta caryophyllene, pinene, limonene, terpinolene, humulene, nerolidol, linalool, ocimene, guaiol, bisabolol, alpha phellandrene, cadinene, camphene, camphor, citral, citronellol, delta 3-carene, eucalyptol, eugenol, gamma terpinene, geraniol, humulene, nerol, nerolidol, ocimene, para-cymene, phytol, pulegone, terpineol, valencene, mixtures thereof and pharmaceutically acceptable salts thereof.

25. Giant multi-lamellar vesicles consisting of deoiled lecithin, wherein the lecithin comprises phosphatidylcholines (PC) and phosphatidylethanolamines (PE) with a PC:PE molar or mass ratio of greater than 1, 5-25% by wt PE and less than 10% by wt phosphatidic acids, and wherein the vesicles are 3-10 μm in size.

26. The vesicles of claim 1, wherein the phospholipid content of the vesicles is greater than 50% by weight.

27. The multi-lamellar vesicles of claim 25, wherein the phospholipid content of the vesicles is greater than 50% by weight.

* * * * *